United States Patent
Pearce et al.

(10) Patent No.: US 12,008,162 B2
(45) Date of Patent: Jun. 11, 2024

(54) ASYNCHRONOUS BRAIN COMPUTER INTERFACE IN AR USING STEADY-STATE MOTION VISUAL EVOKED POTENTIAL

(71) Applicant: Cognixion Corporation, Santa Barbara, CA (US)

(72) Inventors: Sarah Pearce, Burlington (CA); Aravind Ravi, Mississauga (CA); Jing Lu, Mississauga (CA); Ning Jiang, Chengdu (CN); Andreas Forsland, Santa Barbara, CA (US); Chris Ullrich, Ventura, CA (US)

(73) Assignee: COGNIXION CORPORATION, Santa Barbara, CA (US)

(*) Notice: Subject to any disclaimer, the term of this patent is extended or adjusted under 35 U.S.C. 154(b) by 245 days.

(21) Appl. No.: 17/713,622

(22) Filed: Apr. 5, 2022

(65) Prior Publication Data
US 2022/0326771 A1   Oct. 13, 2022

Related U.S. Application Data

(60) Provisional application No. 63/170,987, filed on Apr. 5, 2021.

(51) Int. Cl.
*G06F 3/01* (2006.01)
*H04L 67/131* (2022.01)
*A61B 5/291* (2021.01)

(52) U.S. Cl.
CPC ........... *G06F 3/015* (2013.01); *H04L 67/131* (2022.05); *A61B 5/291* (2021.01); *G06F 2218/12* (2023.01)

(58) Field of Classification Search
CPC ... G06F 3/015; G06F 2218/12; H04L 67/131; A61B 5/291
USPC ........................................................ 345/156
See application file for complete search history.

(56) References Cited

U.S. PATENT DOCUMENTS

| | | | |
|---|---|---|---|
| 10,993,673 B2* | 5/2021 | Natarajan | A61B 5/7278 |
| 2019/0073605 A1* | 3/2019 | Keller | A61B 5/291 |
| 2019/0387998 A1* | 12/2019 | Garten | A61B 5/165 |
| 2020/0337625 A1* | 10/2020 | Aimone | A61B 5/7267 |

OTHER PUBLICATIONS

PCT/IB2022/053179_FSP1996PCT_Written Opinion_dated Jun. 1, 2023.

(Continued)

*Primary Examiner* — Calvin C Ma
(74) *Attorney, Agent, or Firm* — Rowan TELS LLC

(57) ABSTRACT

A method and system are disclosed using steady-state motion visual evoked potential stimuli in an augmented reality environment. Requested stimuli data are received from a user application on a smart device. Sensor data and other context data are also received, where other context data includes data that is un-sensed. The requested stimuli data are transformed into modified stimuli based on the sensor data, and the other context data. Modified stimuli and environmental stimuli are presented to the user with a rendering device configured to mix the modified stimuli and the environmental stimuli, thereby resulting in rendered stimuli. Biosignals generated in response to the rendered stimuli are received from the user to a wearable biosignal sensing device. Received biosignals are classified based on the modified stimuli, resulting in a classified selection, which is returned to the user application.

20 Claims, 19 Drawing Sheets

(56) References Cited

OTHER PUBLICATIONS

R Zerafa et al., The effect of distractors on SSVEP-based brain-computer interfaces, Biomed. Phys. Eng. Express, 2019, pp. 1-13.
Yufeng Ke et al., An online SSVEP-BCI system in an optical see-through augmented reality environment, J. Neural Eng, 2020, pp. 1-17.
Nakanishi Masaki et al: "Integrated interference frequency components elicited by monitor refresh rate to enhance frequency detection of SSVEPs", 2013 6th International ieee/embs Conference on Neural Engineering (NER), IEEE, Nov. 6, 2013 (Nov. 6, 2013), pp. 1092-1095, XP032538379, ISSN: 1948-3546, DOI: 10.1109/NER. 2013.6696127, [retrieved on Dec. 26, 2013].
Nicholas Waytowich et al: "Compact convolutional neural networks for classification of asynchronous steady-state visual evoked potentials", Journal of Neural Engineering, Institute of Physics Publishing, Bristol, GB, vol. 15, No. 6, Oct. 31, 2018 (Oct. 31, 2018), p. 66031, XP020332501, ISSN: 1741-2552, DOI: 10.1088/1741-2552/AAE5D8 [retrieved on Oct. 31, 2018].
PCT/IB2022/053179_FSP1996PCT_International Search Report_ dated Jun. 23, 2022.
PCT/IB2022/053179_FSP1996PCT_Written Opinion of International Searching Authority U.S. Appl. No. 17/713,622_dated Jun. 23, 2022.
Ravi Aravind et al: "A Convolutional Neural Network for Enhancing the Detection of SSVEP in the Presence of Competing Stimuli", 2019 41st Annual International Conference of the IEEE Engineering in Medicine and Biology Society (EMBC), IEEE, Jul. 23, 2019 (Jul. 23, 2019), pp. 6323-6326, XP033625728, DOI: 10.1109/EMBC. 2019.8857822, [retrieved on Oct. 2, 2019].
Rejer Izabela et al: "How to identify the user specific stimulation frequencies for SSVEP-based BCI", 2016 IEEE International Conference on Systems, MAN, and Cybernetics (SMC), IEEE, Oct. 9, 2016 (Oct. 9, 2016), pp. 2750-2755, XP033060559, DOI: 10.1109/SMC.2016.7844655, [retrieved on Feb. 6, 2017].
Vernon J Lawhern et al: "EEGNet: a compact convolutional neural network for EEG-based brain-computer interfaces", Journal of Neural Engineering, Institute of Physics Publishing, Bristol, GB, vol. 15, No. 5, Jul. 27, 2018 (Jul. 27, 2018), p. 56013, XP020330961, ISSN: 1741-2552, DOI: 10.1088/1741-2552/AACE8C. [retrieved on Jul. 27, 2018].
Zhao Xincan et al: "SSVEP Stimulus Layout Effect on Accuracy of Brain-Computer Interfaces in Augmented Reality Glasses", IEEE Access, IEEE, USA, vol. 8, Jan. 1, 2020 (Jan. 1, 2020), pp. 5990-5998, XP011764809, DOI: 10.1109/ ACCESS.2019.2963442 [retrieved on Jan. 1, 2020 O].

\* cited by examiner

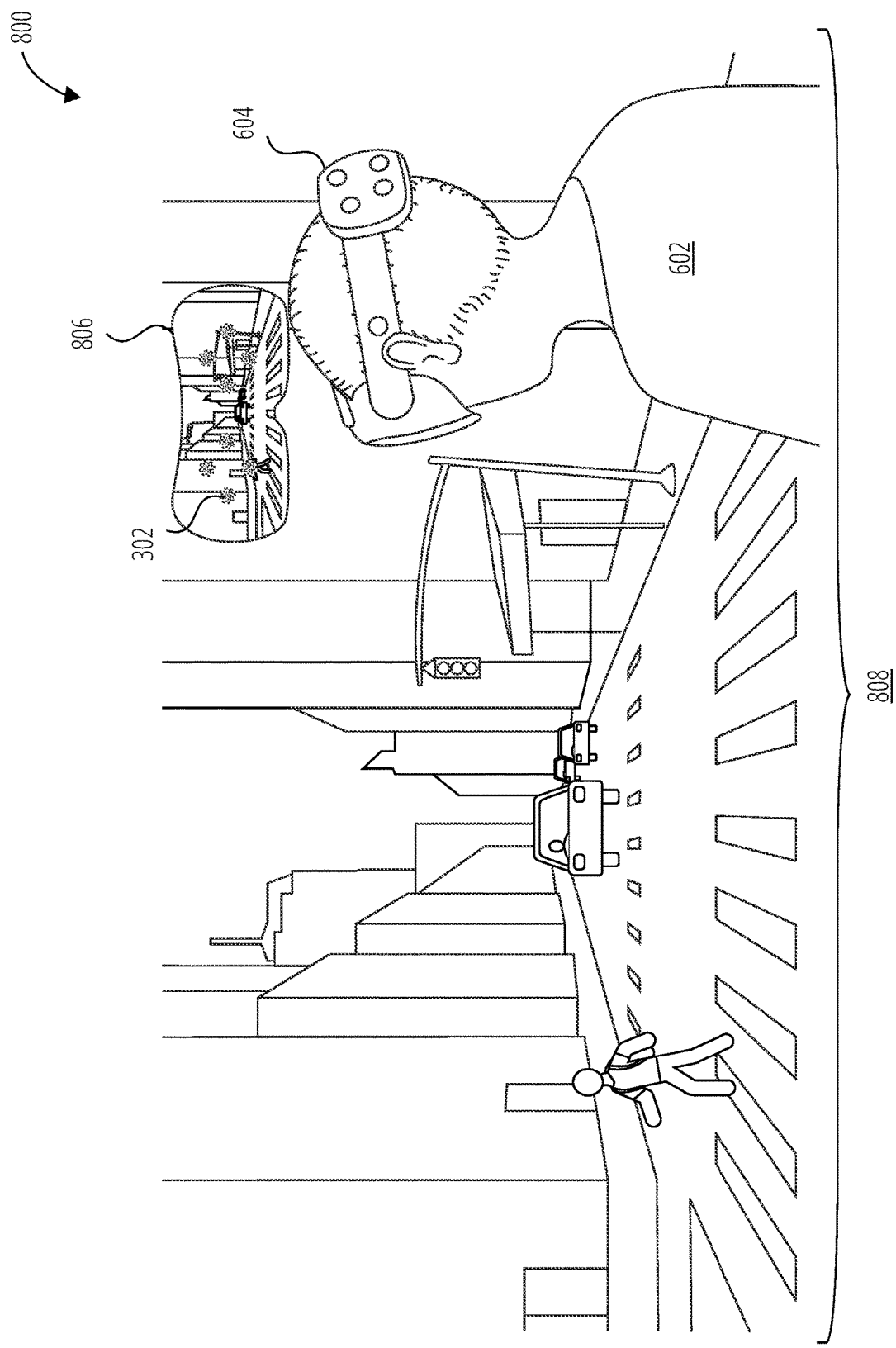

ASYNCHRONOUS BRAIN COMPUTER INTERFACE IN AR USING STEADY-STATE MOTION VISUAL EVOKED POTENTIAL

CROSS-REFERENCE TO RELATED APPLICATIONS

This application claims the benefit of U.S. provisional patent application Ser. No. 63/170,987, filed on Apr. 5, 2021, the contents of which are incorporated herein by reference in their entirety.

BACKGROUND

Electroencephalography-based brain computer interfaces (BCIs) enable humans to establish a direct communication pathway between the brain and the external environment bypassing the peripheral nerves and muscles. Steady-state visually evoked potential (SSVEP) based BCIs are dependent or reactive BCIs that detect electroencephalogram (EEG) responses to repetitive visual stimuli with distinguishable characteristics (e.g., different frequencies). The BCI may determine which stimulus occupies the user's visual attention by detecting the SSVEP response at the targeted stimulus frequency from an EEG recorded at the occipital and parieto-occipital cortex. This may appear as a significant peak at the targeted stimulus frequency and potentially at its higher-order harmonics or subharmonics.

Traditionally, these stimuli are mostly presented on a computer screen. However, augmented reality (AR) and virtual reality (VR) devices may allow users to view repetitive visual stimuli and their external surroundings in the same field of view providing an enhanced user experience. Several studies have investigated the AR approach based on using a video see-through (VST) based head-mounted display (HMD) combined with SSVEP. These studies have applied AR-BCI for applications such as gaming, navigation in a 3D space, quadcopter control, etc., where the real-world scene is acquired using a camera placed on top of the HMD and displayed within the VR environment.

The SSVEP stimuli are most commonly designed as a monochromatic object whose intensity is modulated at a fixed frequency. As a result, it appears as a flashing object to the user. This flashing stimulus may induce visual fatigue and discomfort. As a consequence, this decreases the overall signal-to-noise ratio (SNR), decoding performance, and interactivity of the BCI. Furthermore, the presentation of these stimuli on a computer screen or other opaque medium in conventional configurations limits the application scenario of the system in a potential augmented reality AR application. In a real-world environment, users may need to shift their visual attention back and forth between the stimulus presentation on a monitor and their normal visual field, which may contain a multitude of distracting or confounding visual stimuli, further impacting the SNR in resultant EEG readings and potentially reducing the accuracy of BCI determinations of viewer gaze and attention. The VST based HMDs that offer this capability, however, provide a limited field of view, largely restricted by the camera.

There is, therefore, a need for a method and system capable of testing, training, and implementing visual stimuli that perform the functions of SSVEP stimuli in inducing a BCI response, while reducing visual fatigue and discomfort in a viewer and improving signal to noise ratio, decoding performance, and interactivity of a BCI for use in VR/AR applications. There is additionally a need to test, train, and implement these stimuli in an environment and with equipment more closely resembling a real-world user AR/VR application. Further there is a need for systems that are capable of testing, training and implementing other stimuli such as audio or somatosensory evoked potential stimuli which are also known to produce classifiable EEG signals.

BRIEF SUMMARY

In one aspect, a method includes receiving one or more requested stimuli data from a user application on a smart device, receiving at least one of sensor data and other context data, where the other context data includes data that is un-sensed, transforming at least a portion of the requested stimuli data, into modified stimuli, based at least in part on at least one of the sensor data and the other context data, presenting the modified stimuli and environmental stimuli to the user with a rendering device configured to mix the modified stimuli and the environmental stimuli, thereby resulting in rendered stimuli, receiving biosignals from the user, generated in response to the rendered stimuli, on a wearable biosignal sensing device, classifying the received biosignals using a classifier based on the modified stimuli, resulting in a classified selection, and returning the classified selection to the user application.

In one aspect, a system comprising a smart device; a rendering device; a wearable biosignal sensing device on a user; a processor; and a memory storing instructions that, when executed by the processor, configure the system to execute the above-described method.

In one aspect, a method includes receiving one or more requested stimuli data from a user application on a smart device. The method also includes receiving at least one of sensor data and other context data, where the other context data includes data that is un-sensed. The method then includes transforming at least a portion of the requested stimuli data into modified stimuli, based at least in part on at least one of the sensor data and the other context data, where the modified stimuli include steady-state motion visually evoked potential stimuli, as well as other evoked potentials. The method includes presenting the modified stimuli and environmental stimuli to the user with a rendering device configured to mix the modified stimuli and the environmental stimuli, thereby resulting in rendered stimuli, where this includes at least one of using at least one of a visual device, a haptic device, and an auditory device sensed by the user and rendering the modified stimuli and environmental stimuli on an augmented reality optical see-through (AR-OST) device associated with the smart device. The method then includes receiving biosignals from the user, generated in response to the rendered stimuli, on a wearable biosignal sensing device. The method further includes determining whether to send the biosignals to a classifier by using at least one of the existence or absence of an intentional control signal, where determination of the existence of the intentional control signal includes at least one of detecting a manual intention override signal from the smart device, and determining, at least in part, from received biosignals that the user is intending to fixate on at least one of the rendered stimuli. On condition the intentional control signal exists, the method includes sending the received biosignals, to the classifier. On condition the intentional control signal is absent, the method includes continuing to receive received biosignals from the user. The method then includes classifying the received biosignals using the classifier based on the modified stimuli, resulting in a classified selection. The method finally includes returning the classified selection to the user application.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 8A-FIG. 8C illustrate projections for SSMVEP BCI use with AR-OST 800 in accordance with one embodiment.

FIG. 11A illustrates SSVEP 8 Hz results 1100*a*.
FIG. 11B illustrates SSMVEP 8 Hz results 1100*b*.
FIG. 11C illustrates SSVEP 10 Hz results 1100*c*.
FIG. 11D illustrates SSMVEP 10 Hz results 1100*d*.
FIG. 11E illustrates SSVEP 12 Hz results 1100*e*.
FIG. 11F illustrates SSMVEP 12 Hz results 1100*f*.
FIG. 11G illustrates SSVEP 15 Hz results 1100*g*.
FIG. 11H illustrates SSMVEP 15 Hz results 1100*h*.

DETAILED DESCRIPTION

A steady-state motion visually evoked potential (SSMVEP) based BCI addresses the drawbacks of SSVEP BCI use, including fatigue, visual discomfort, and relatively low interactive performance of the BCI. In contrast with the flashing style of SSVEP stimuli, the SSMVEP stimuli are designed to elicit visually perceived movement. In one embodiment, this design may include an equal-luminance black and white radial checkerboard, which may be modulated at a fixed frequency. Specifically, this movement pattern may include a radial contraction and expansion of the stimulus. SSMVEP BCIs include the advantages of SSVEP BCI, such as high SNR, high information transfer rate (ITR), and low participant training time compared to other types of BCIs while minimizing SSVEP-related discomfort for operators. The SSMVEP stimuli may be presented via an AR/VR HMD. A portable EEG system may be used alongside or incorporated within the AR HMD, making AR/VR-based BCIs a promising approach to implementing BCIs outside of research lab settings and realizing practical real-world applications. Optical see-through (OST) based HMDs may offer an improvement over the VST HMDs conventionally used to provide an overlay of stimuli onto real-world environmental visual stimuli. OST AR devices may comprise a semi-transparent screen or an optical element. Virtual content such as generated stimuli may be directly displayed on the screen, overlaid on the user's normal field of view, and the environmental stimuli present within that field. In one embodiment, a novel AR-OST based BCI system may further address the challenges of current SSVEP systems. The AR-OST based BCI system may use a four-target SSMVEP BCI such as is disclosed herein.

Users may interact with a BCI in an asynchronous manner whenever they want. This means the BCI may not be dependent on the precise stimulus timing or predefined time frames. Compared to a cue-paced or synchronous BCI, asynchronous operation may involve continuous decoding and analysis of the response. This operation may be more technically demanding but may offer a more natural form of interaction. During asynchronous interaction, operation may involve two states: an intentional control (IC) state and a no control (NC) state. "IC state" in this disclosure refers to the time when a user is detected, determined, or assumed to be gazing at a generated stimulus. "NC state" in this disclosure refers to a rest state, or the time when a user detected, determined, or assumed to not be gazing at a generated stimulus. Convolutional neural network (CNN) based methods may be used in asynchronous classification of SSMVEP BCIs, and may perform with improved accuracy and efficiency compared to more traditional classification algorithms. The offline decoding performance of the BCI system may be evaluated using a Complex Spectrum CNN (C-CNN) for data processed in an asynchronous manner.

Figure 1:
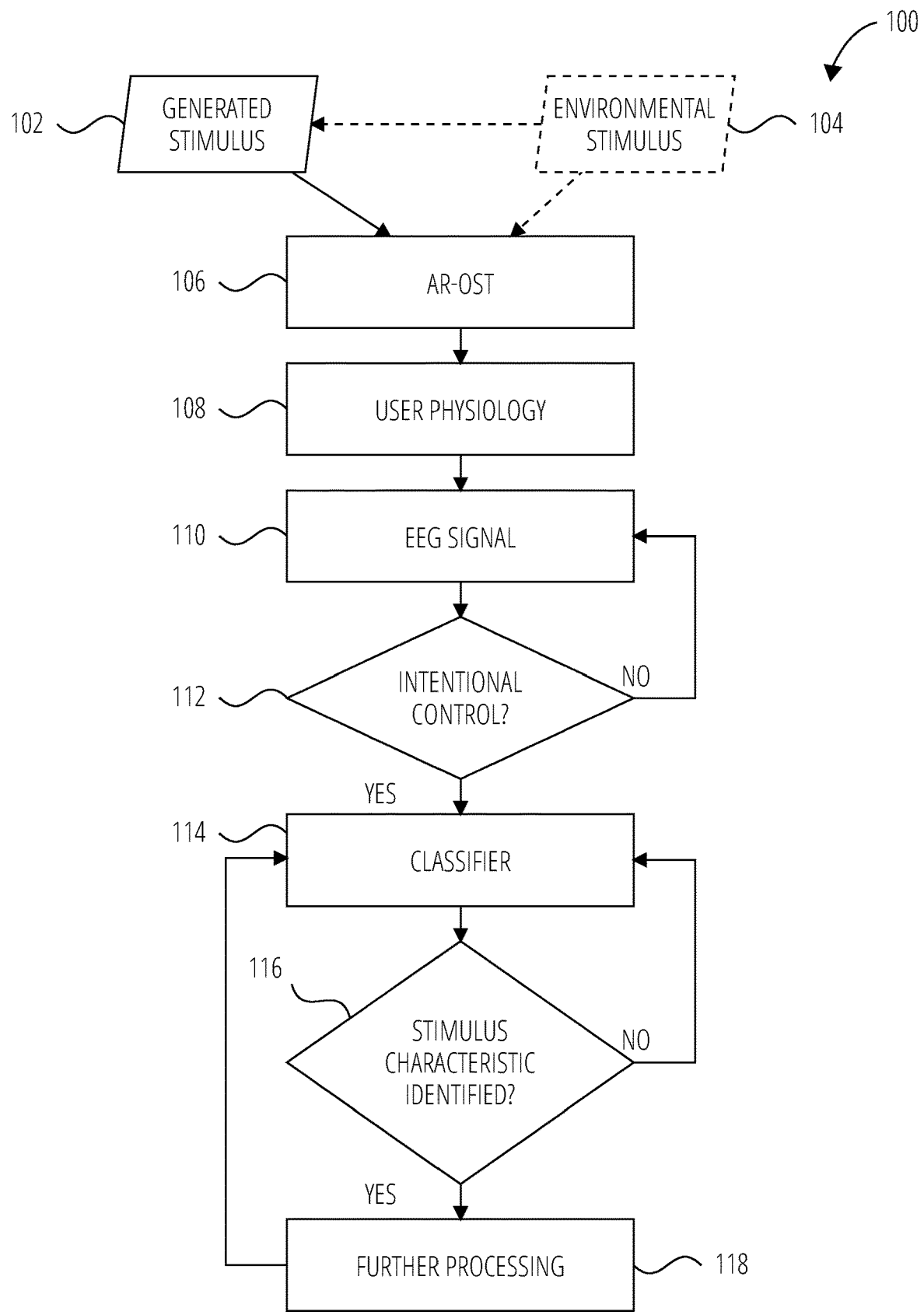
FIG. 1 illustrates a process for using SSMVEP BCI 100 in accordance with one embodiment.

FIG. 1 illustrates a process for using SSMVEP BCI 100 in accordance with one embodiment. The process for using SSMVEP BCI 100 begins by providing an SSMVEP generated stimulus 102 to an AR-OST in block 106. "Generated stimulus" in this disclosure refers to a predefined or dynamically determined perceptible entity presented to a BCI user by action of a computer, AR/VR headset, or other similar device. In one application, the generated stimulus may be an icon-type digital graphic projected into the user's field of view. The perception of such stimuli by the user may result in changes in the user's EEG pattern as detected and analyzed by a BCI. In some applications, the EEG pattern changes induced by the user sensing the generated stimulus may be interpreted as indicating a selection, decision, or action intended by the user.

In one embodiment, the user may be insulated from one or more types of environmental stimulus. This may be for experimental purposes in determining the robustness of a BCI against interference from environmental stimuli, in order to provide a baseline reading for comparison. In another embodiment, environmental stimuli may be blocked for reasons specific to that use case. In another embodiment, an environmental stimulus 104 may be provided to or through an AR-OST at block 106 in addition to the SSMVEP generated stimulus 102. "Environmental stimulus" in this disclosure refers to a visual, auditory, tactile, olfactory, or other stimulus external to and perceptible in the environment around a BCI user. The perception of such stimuli by the user may result in changes in the user's EEG pattern as detected and analyzed by the BCI. Because environmental stimuli 104 may impact a user's EEG pattern, and because such impact may compete or conflict with the impact from SSMVEP generated stimuli 102, environmental stimuli 104 may be considered confounders that may cause interference and reduce a BCI's ability to interpret a user's interaction with an SSMVEP generated stimulus 102.

Thus, in one embodiment, environmental stimuli 104 may be used to modulate the SSMVEP generated stimuli 102 presented to the AR-OST in block 106. For example, if a flashing light is detected in the user's environment, and the light is flashing at a frequency near a frequency of display alteration associated with a default generated stimulus, the SSMVEP generated stimulus 102 presented may be presented with some other frequency of alteration, such that a BCI may not be confounded in frequency-based interpretation of the user's detected brain activity. Other environmental data, such as time of day, location, etc., may also be used to modulate the presented SSMVEP generated stimuli 102 to improve reliability of the BCI performance in interpreting user intention from interaction with the SSMVEP generated stimulus 102 amid a number of environmental stimuli 104.

At block 106, the AR-OST may present the SSMVEP generated stimulus 102 and environmental stimulus 104 to a user. The AR-OST may be a computerized system that is capable of passing through environmental stimuli while simultaneously programmatically generating and presenting novel stimuli. In one embodiment, this may be an AR headset with a visor containing lenses that allow the user to perceive visually the environment around them, thus providing the environmental stimulus 104 to the user. The lenses may in one embodiment comprise a transparent organic light-emitting device (TOLED) capable of emitting light to produce a generated stimulus for a user. In another embodiment, the lenses may be reflective on an interior face to a degree that does not interfere with visibility of the environment to a wearer, while able to reflect imagery projected from a device outside the wearer's field of view, but within the visor behind the lenses. In such an embodiment, the visor may comprise a gap or slit for insertion of a smart device such as a smartphone. The SSMVEP generated stimulus 102 may be created by the display of the smartphone and reflected back to the user by the lenses of the AR-OST.

The SSMVEP generated stimulus 102 and environmental stimulus 104 presented on to or through the AR-OST in block 106 may then be transmitted to a user's physiology in block 108. "User physiology" in this disclosure refers to a user's sensation and perception apparatus and typically includes mediating tissues, peripheral nerves, and the central nervous system. For optical stimuli, this includes the eye tissue, retina, and occipital lobes. User physiology may be the pathway along which the SSMVEP generated stimulus 102 and environmental stimulus 104 reach and affect the user's brain as neuroelectric signals that may be detected by sensors such as EEG contacts.

EEG Signals may be detected in block 108 by these EEG contacts. One or more EEG signals may be obtained in this manner through non-invasive contact with the user's skull. In one embodiment, these signals may be obtained invasively. In another embodiment, EEG signals may be obtained using a mixture of invasive and non-invasive sensors.

At decision block 112, a BCI monitoring and analyzing EEG signals may determine whether the EEG signals detected represent the user participating in an IC state or an NC state. If no intentional control is determined or detected, the BCI may return to monitoring EEG signals at block 110. If the BCI determines or detects intentional control on the part of the user, the process for using SSMVEP BCI 100 may proceed to the classifier in block 114. In one embodiment, an IC state may be determined to occur when a stimulus is presented, the NC state being determined as occurring when no stimulus is presented. In another embodiment, gaze tracking performed by cameras or additional sensors incorporated into an AR/VR headset or other configuration may be used to detect a user's focus as being on a provided stimulus, which may be used to indicate that the user is interacting in the IC state. In another embodiment, the transition between overt and covert sensing of the stimuli may be detected in the EEG data and used to determine eye focus and intention. This step may be determined by processing external to the BCI in one embodiment. No training may be needed to incorporate this determination or detection into BCI analysis. In another embodiment, the intention detection may be determined by a heuristic programmed into the device or retrieved from the cloud. In another embodiment, the intention detection occurs in a classifier, which may be part of a neural network specifically trained for intention detection.

At block 114 a classifier may be invoked to characterize detected EEG signals. The classifier may evaluate whether the EEG signals correspond to one or more of the SSMVEP generated stimuli 102. An array of values may be generated within the range from 0 to 1 expressing the probability of the stimulus being present. In some embodiments, a softmax algorithm or selection process may choose a single element from the classifier output. If at decision block 116 a stimulus characteristic is not detected, the process for using SSMVEP BCI 100 may return to block 114. In some embodiments, the array of generated values may be provided to further processing without a specific classification decision.

If a stimulus characteristic is detected at decision block 116, the process for using SSMVEP BCI 100 may proceed to perform further processing (block 118). Further processing may in one embodiment include refinement of classifier algorithms and updating the classifier at block 114 with these refinements to improve the performance of the BCI.

In one embodiment, the spatial and temporal frequencies of motion for the SSMVEP generated stimulus 102 may be modulated based on distribution of spatial and temporal confounders sensed from the environmental stimulus 104. In this way, the SSMVEP generators may maximize robustness regardless of ambient stimulus. In another embodiment, a set of SSMVEP generated stimulus 102 may be analyzed to extract their principal visual frequencies. These frequencies may then be used during EEG signal analysis to classify user attention (e.g., IC state versus NC state). In another embodiment, a set of SSMVEP generated stimuli 102 may be analyzed to calculate their principal spatial frequencies. During visual presentation, the animation rate may be modified to increase or decrease the stimuli update such that specific temporal frequencies are generated. These frequencies may be chosen to be maximally distinct from ambient frequencies and/or frequencies of environmental stimuli 104 or other simultaneously presented stimuli (spatial or temporal). In another embodiment, the temporal frequency may be modulated using an orthogonal coding scheme, pseudo-random sequence, or other deterministic generative modulation.

Figure 2A:
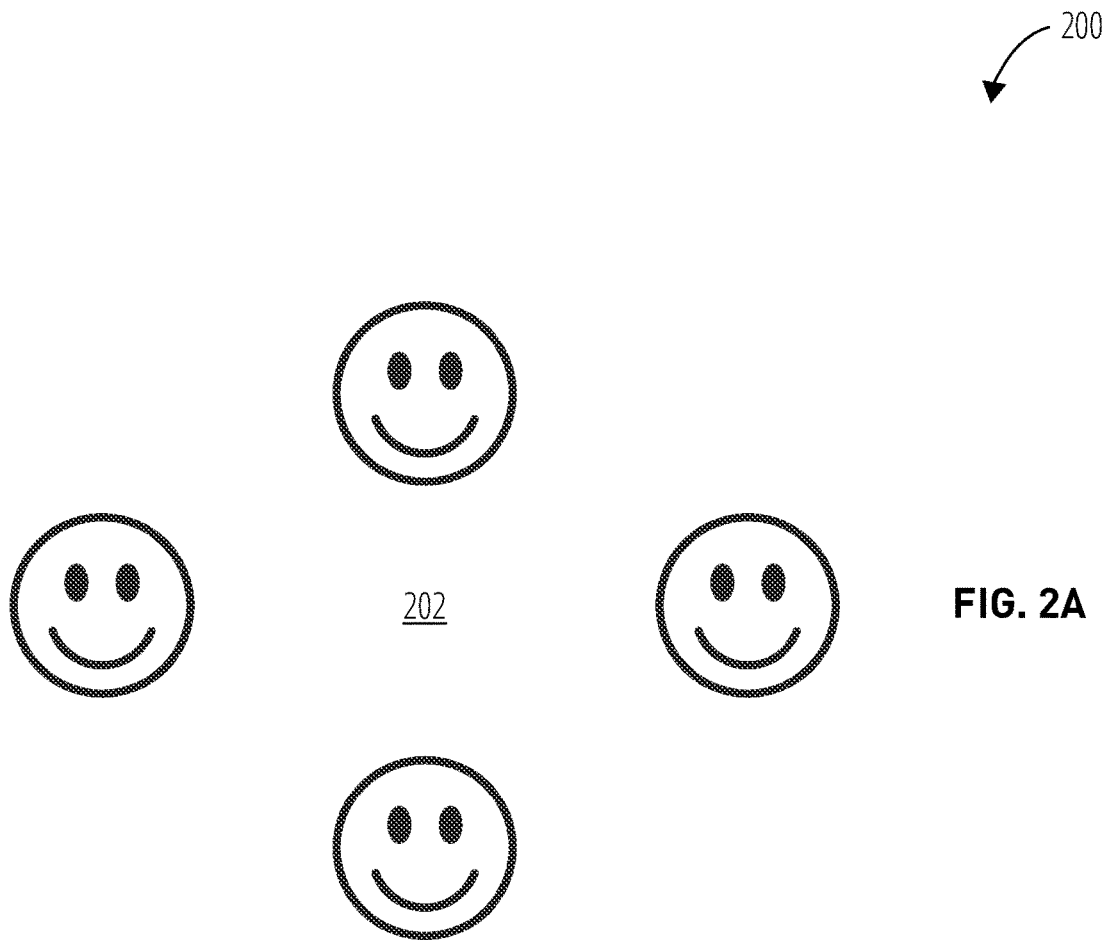
FIG. 2A and FIG. 2B illustrate an exemplary SSVEP pattern and variation 200.
Figure 2B:
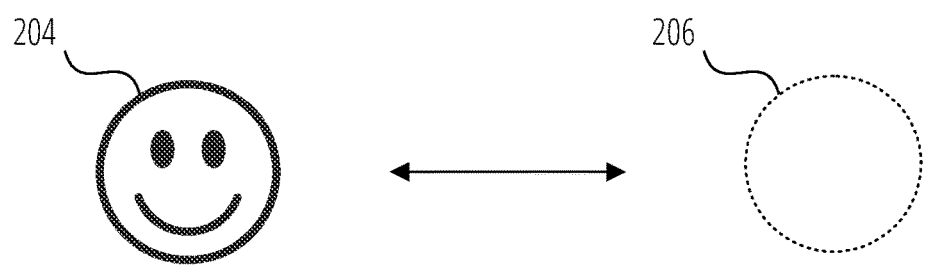

FIG. 2A and FIG. 2B illustrate an exemplary SSVEP pattern and variation 200. Four SSVEP stimuli may be arranged in a base SSVEP pattern 202 as shown in FIG. 2A. An emoji may be used as a flashing SSVEP stimulus. In one embodiment, this may be a circular emoji as illustrated, but any shape emoji known by one of skill in the art may be used. This type of SSVEP stimulus may provide a more realistic and engaging stimulus compared to a conventional monochromatic, colored, circular stimulus.

Each of the SSVEP stimuli in the pattern may correspond to a different frequency of change. For example, one stimulus may transition between an on and off state, as indicated by SSVEP image on 204 and SSVEP image off 206 in FIG. 2B. Flicker (on/off) frequencies of 8 Hz, 10 Hz, 12 Hz, and 15 Hz, may each be applied to one of the SSVEP stimuli in the base SSVEP pattern 202.

Figure 3A:
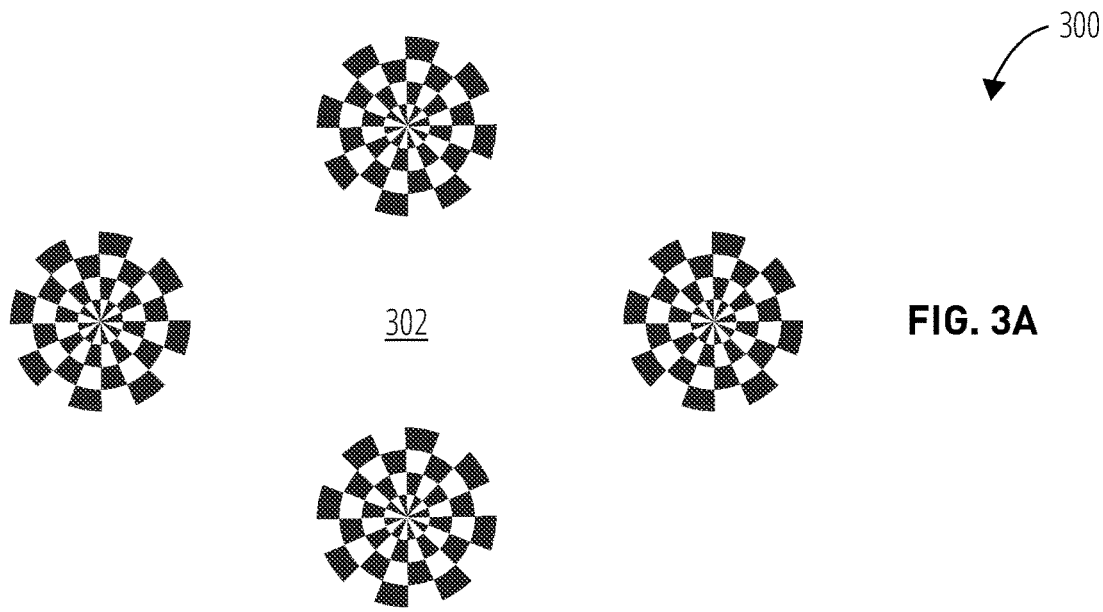
FIG. 3A-FIG. 3D illustrate an exemplary SSMVEP pattern and variations 300 in accordance with one embodiment.

FIG. 3A-FIG. 3D illustrate an exemplary SSMVEP pattern and variations 300 in accordance with one embodiment. The base SSMVEP pattern 302 as illustrated in FIG. 3A may comprise the same four-stimuli arrangement as may be used for the base SSVEP pattern 202 of FIG. 2A. However, a radial checkerboard image may be used as the SSMVEP stimulus. The SSMVEP stimulus is not intended to flash on and off or flicker as the SSVEP stimuli previously discussed but may incorporate repetitive motion. In one embodiment, these repetitive movements may occur with the same 8 Hz, 10 Hz, 12 Hz, and 15 Hz frequencies as described with respect to FIG. 2A and FIG. 2B. In another embodiment, a plurality of distinct stimuli may be rendered to the user. These distinct stimuli may include any combination of SSVEP, radial checkerboard SSMVEP or animated SSMVEP (discussed below).

Figure 3B:
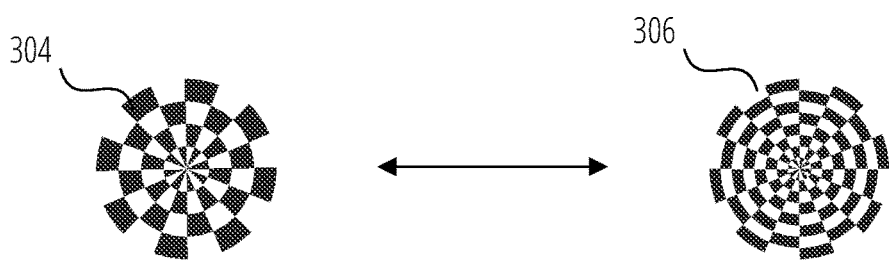
Figure 3C:
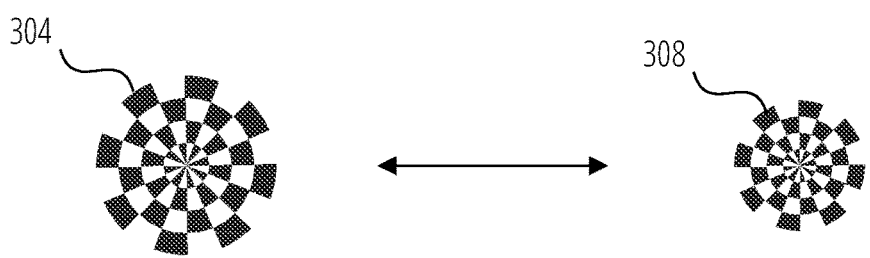
Figure 3D:
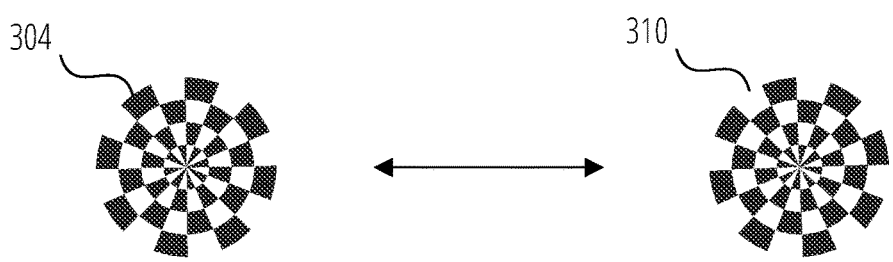

Repetitive movements of the SSMVEP stimuli may take a number of forms. In one embodiment, the base SSMVEP image 304 may transition to an SSMVEP image with a different pattern density 306 and back at the desired frequency, as shown in FIG. 3B. In one embodiment, the base SSMVEP image 304 may transition to an SSMVEP image with a different size 308 and back at the desired frequency as indicated in FIG. 3C. In one embodiment, the base SSMVEP image 304 may transition to a rotated SSMVEP image 310 and back as shown in FIG. 3D at the desired frequency. Other changes to the image representing movement may be contemplated by one skilled in the art.

In another embodiment, the SSMVEP stimuli may be based on repetitive animated graphical sequences such as stickers or emojis that include one or more static images. The SSMVEP stimuli may be generated from the animated sequences by varying the playback rate to generate a specific spatial and/or temporal stimulus frequency, which can be sensed by the BCI.

Figure 4A:
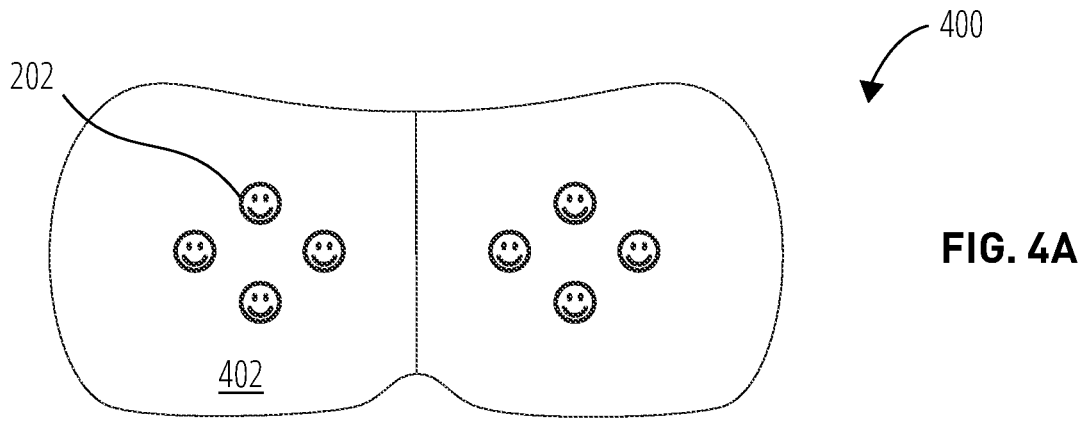
FIG. 4A and FIG. 4B illustrate binocular projections for SSVEP BCI interaction 400.
Figure 4B:
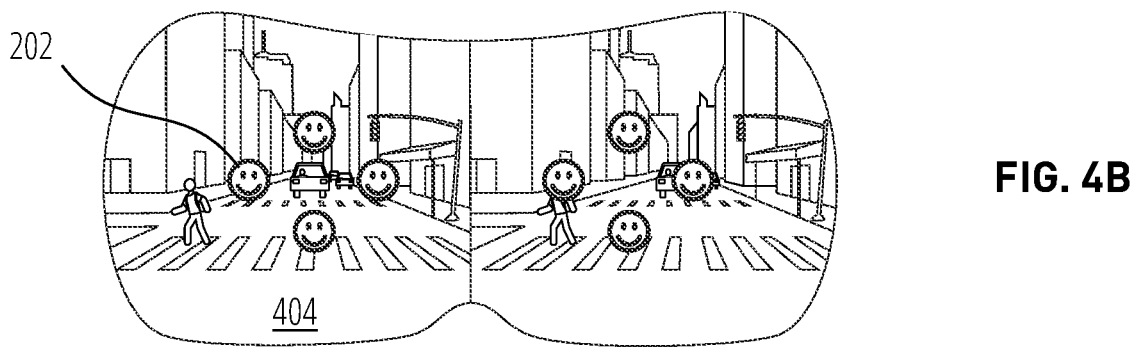

FIG. 4A and FIG. 4B illustrate binocular projections for SSVEP BCI interaction 400. Such projections may be displayed to a user wearing a VST HMD or the novel AR-OST incorporated in the solution disclosed herein. Visual stimuli in the AR headset may be calibrated for an individual user, aligning a center point of an intended display to the center of the field of view of a user.

In one embodiment, as shown in FIG. 4A, a base SSVEP pattern 202 as previously described may be displayed overlaid onto a non-active background 402, such as a plain black background.

In another embodiment, as shown in FIG. 4B, the base SSVEP pattern 202 may be displayed overlaid onto an active background 404. For example, a stereo video of an urban setting playing at thirty frames per second may be used. The video may show a first-person view wherein the camera is mounted in the front of a car navigating through the streets of a typical busy North American urban area.

The four SSVEP stimuli of the base SSVEP pattern 202 may be superimposed on the stereo video and presented in the foreground with the video continuously playing in the background. The video may also show the first-person view as navigating turns and stopping at traffic lights, may contain background sound, and may include point of view movements or pauses at different points in the video.

Figure 5A:
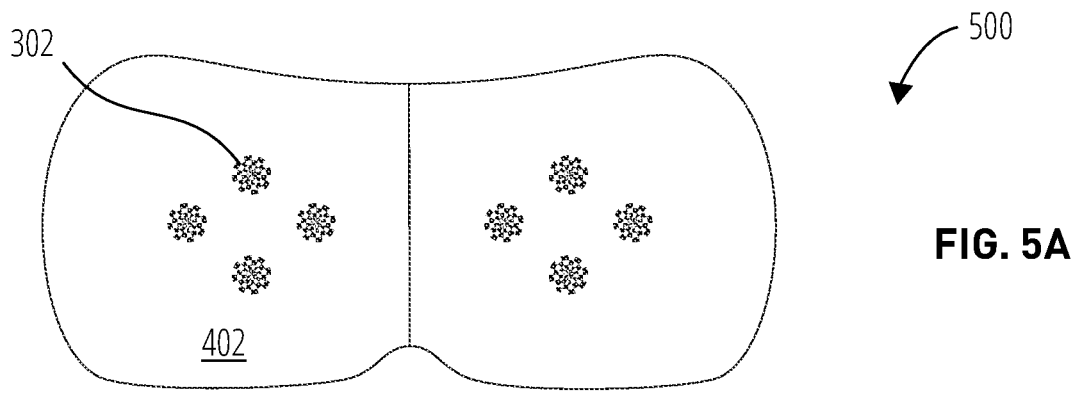
FIG. 5A and FIG. 5B illustrate binocular projections for SSMVEP BCI interaction 500 in accordance with one embodiment.
Figure 5B:
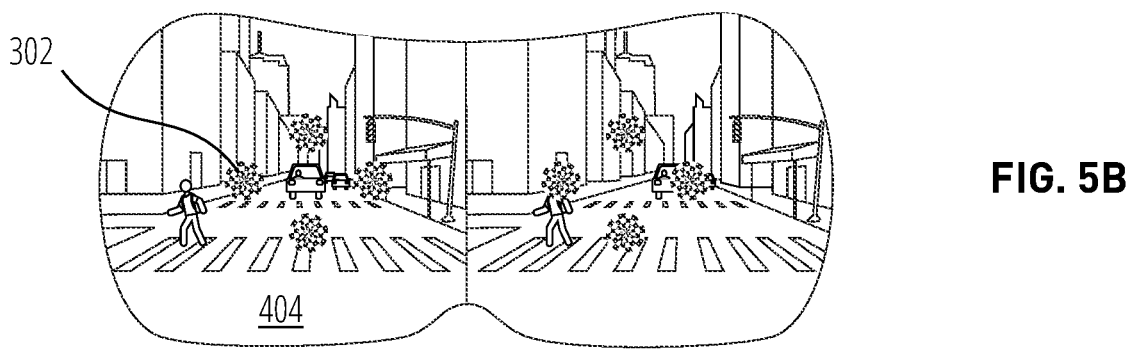

FIG. 5A and FIG. 5B illustrate binocular projections for SSMVEP BCI interaction 500 in accordance with one embodiment. The four SSMVEP stimuli of the base SSMVEP pattern 302 may be superimposed onto a non-active background 402 as shown in FIG. 5A and an active background 404 as shown in FIG. 5B, similar to the configuration described with respect to FIG. 4A and FIG. 4B.

Figure 6:
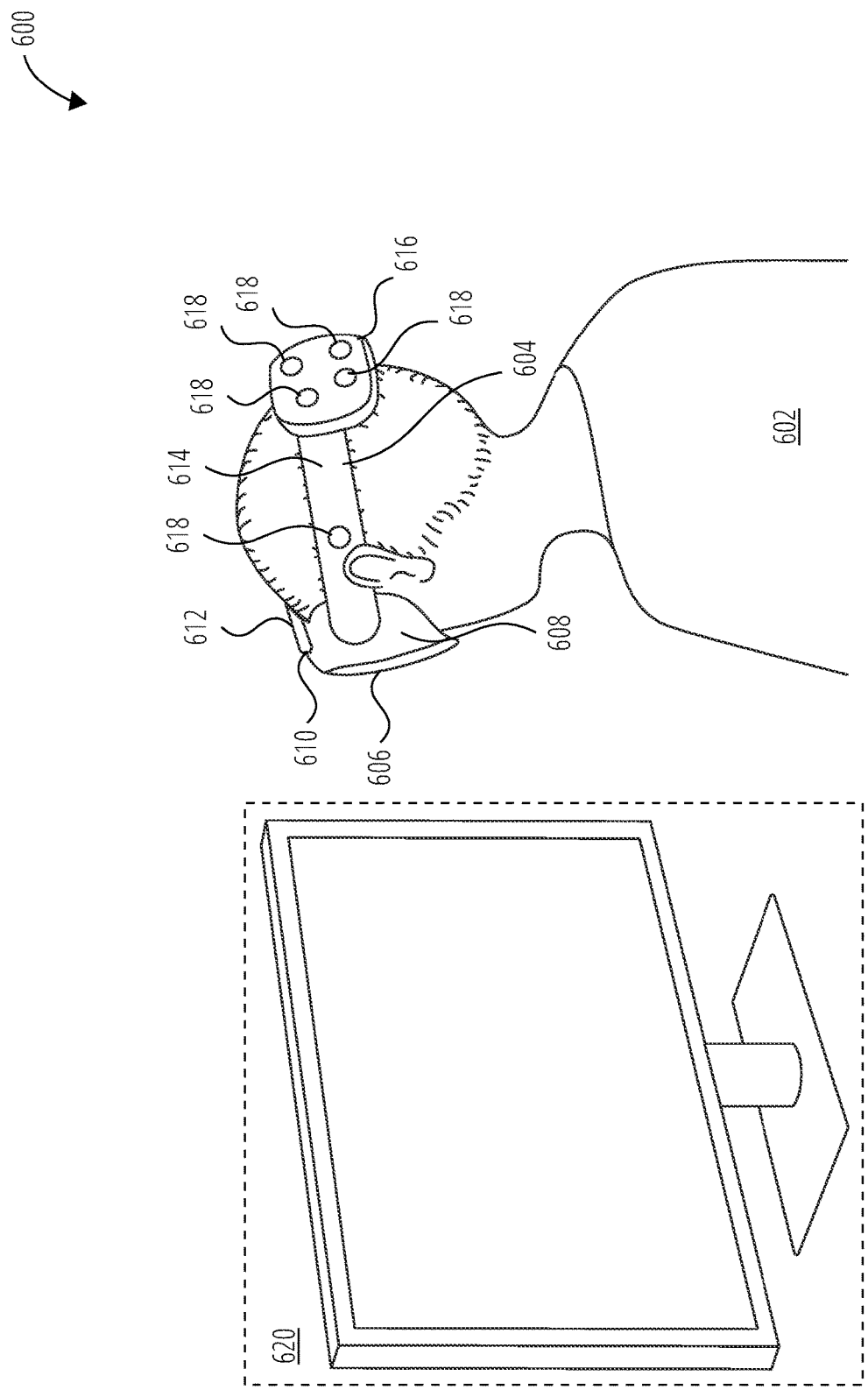
FIG. 6 illustrates an AR-OST BCI configuration 600 in accordance with one embodiment.

FIG. 6 illustrates an AR-OST BCI configuration 600 in accordance with one embodiment. In this configuration, a user 602 may wear an AR-OST 604 comprising a lightweight, optical see-through AR-OST shield 606 which may be partially transparent and, in some embodiments, partially reflective. The AR-OST shield 606 may be held within a frame 608, the frame 608 also including a smart device slot 610 with a smart device 612 inserted. In this manner, images generated on the screen of the smart device 612 may reflect off of the interior of the AR-OST shield 606 and be visible to the user 602. In another embodiment, the AR-OST shield 606 may incorporate an active rendering mechanism, such as a transparent organic light-emitting device (TOLED) capable of mixing OLED rendered visual stimuli with environmental light sources to present a mixed image to the user's eyes. In another embodiment, the AR-OST shield 606 may be fully transparent but the frame 608 may also include the capability to render light directly on the user's retina.

A strap 614 may connect the frame 608 with a compartment accessory or module containing a BCI 616, and a plurality of integrated EEG electrodes 618. In another embodiment, the EEG electrodes 618 may be configured as part of a separate EEG apparatus or other sensor apparatus. The BCI 616 may similarly be configured as a separate computing apparatus. Other sensor apparatuses may include g.USBamp and Gammabox (g.tec Guger Technologies, Austria), used with wet electrodes (g.Scarabeo) to acquire an EEG signal. The AR-OST 604 and smart device 612 may each transmit and receive signals via wired and wireless connections to each other and to additional computing and sensing apparatuses.

Finally, because of the see-through properties of the AR-OST shield 606 of the AR-OST 604, a monitor 620 may be incorporated into the AR-OST BCI configuration 600 in some embodiments, allowing different images to be displayed on the interior of the AR-OST shield 606 as foreground features and on the monitor 620 as background features. In one embodiment, all images may be displayed on the inside of the AR-OST shield 606, and in another, images displayed within the AR-OST shield 606 may overlay a plurality of real-world objects visible in the user's environment. In another embodiment, a selection of the rendered stimuli are presented in the environment, external to the AR-OST 604 wearable apparatus. These external stimuli could be signs, advertisements or other notifications fixed in space.

Figure 7A:
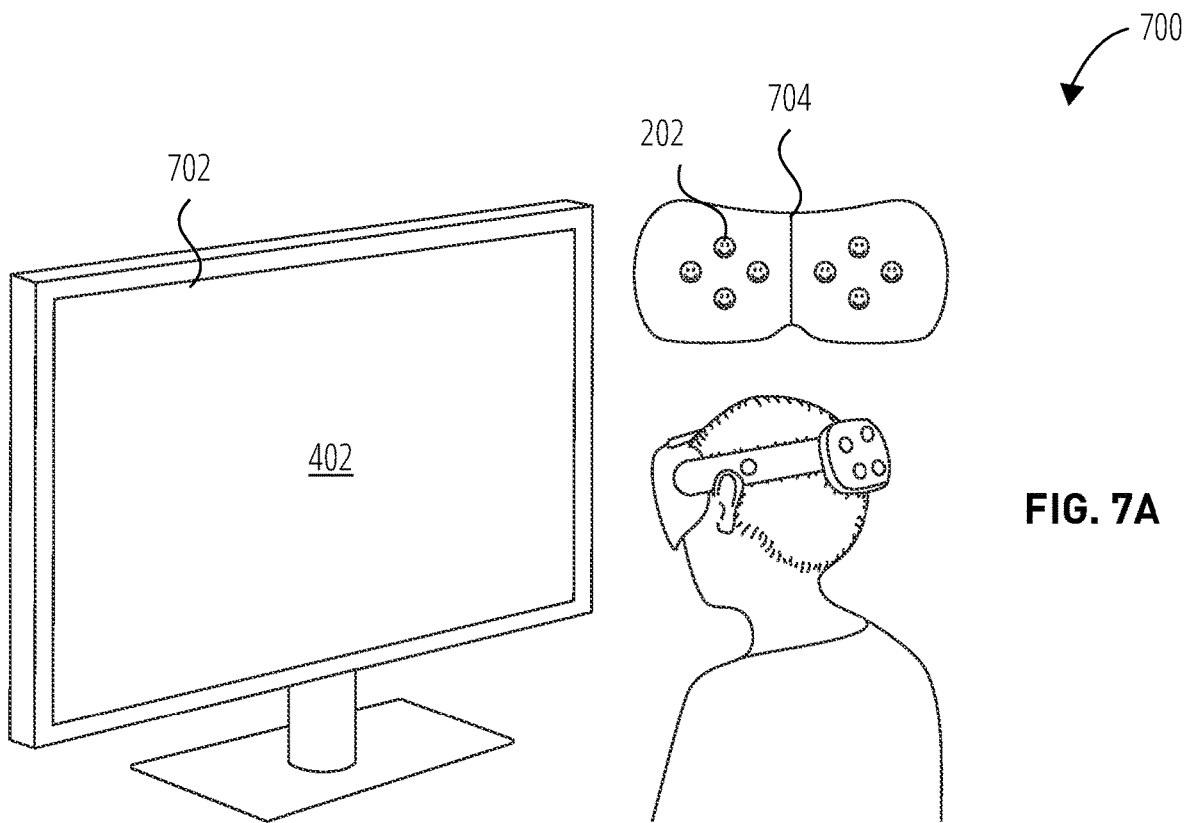
FIG. 7A and FIG. 7B illustrate projections for SSVEP BCI use with AR-OST 700 in accordance with one embodiment.
Figure 7B:
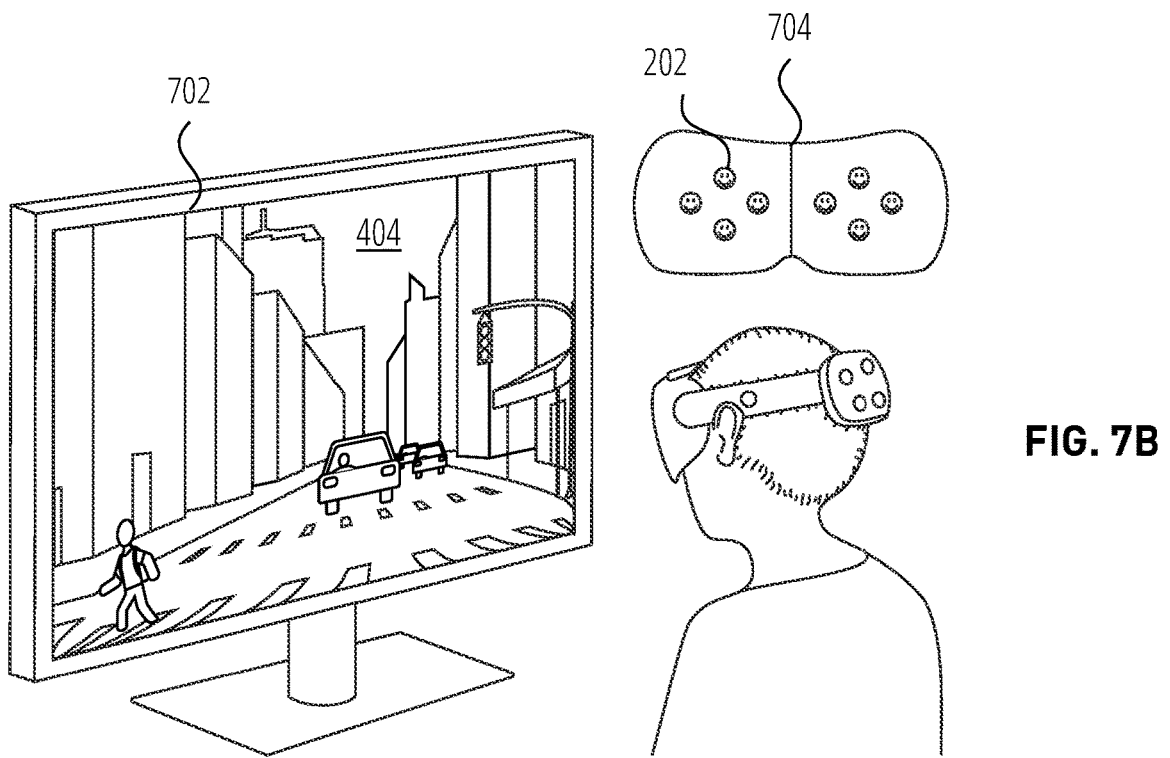

FIG. 7A and FIG. 7B illustrate projections for SSVEP BCI use with AR-OST 700 in accordance with one embodiment. The AR-OST BCI configuration 600 of FIG. 6 may be used to exercise a user's interaction with an AR-OST and BCI using the projections for SSVEP BCI use with AR-OST 700.

In one embodiment, as shown in FIG. 7A, a monitor display 702 may comprise a non-active background 402 previously discussed, such as a black screen. The base SSVEP pattern 202 may be shown as the AR-OST shield display 704. This base SSVEP pattern 202 may be generated by a smart device in place within a smart device slot in the frame as described with respect to FIG. 6. The smart device may comprise an app designed to interact with the SSVEP BCI system or may be paired through a wired or wireless connection with an additional computing device configured to produce the base SSVEP pattern 202 and its variations.

In an alternative embodiment illustrated in FIG. 7B, the monitor display 702 may comprise the active background 404 introduced with respect to FIG. 4B, and the base SSVEP pattern 202 and its variations may again be shown as the AR-OST shield display 704.

Figure 8A:
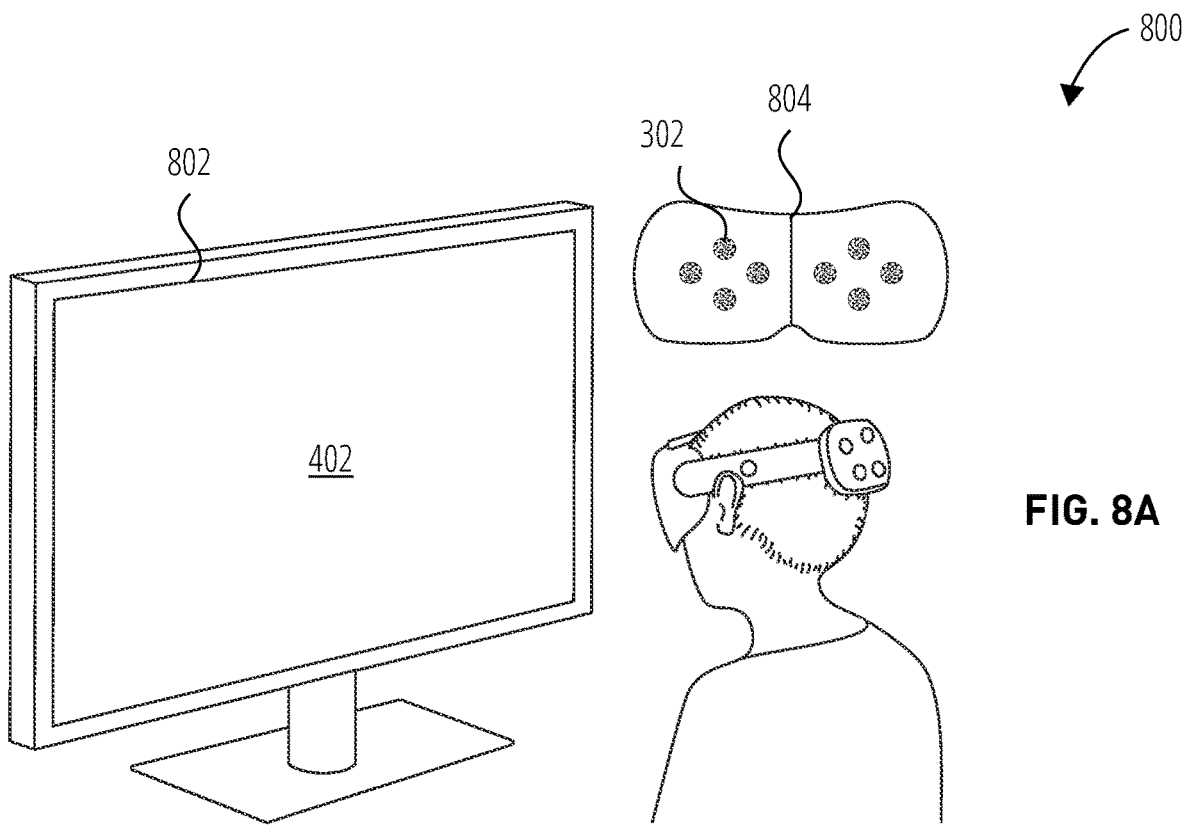
Figure 8B:
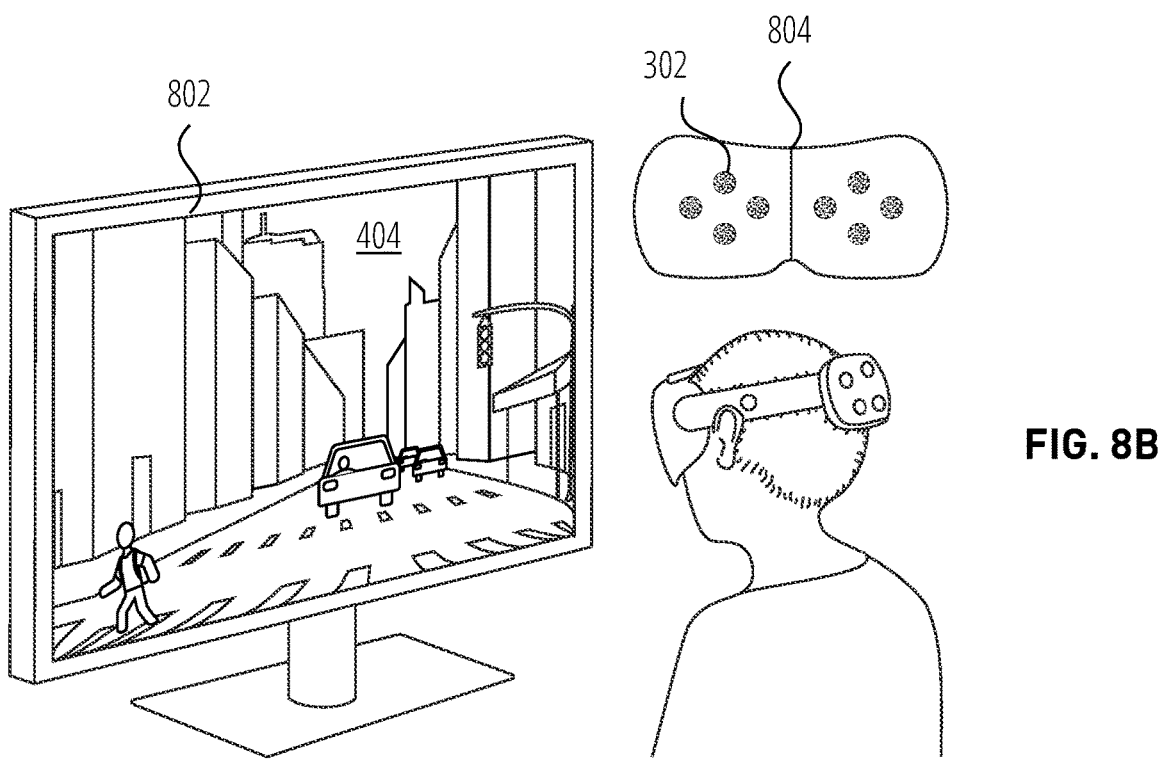

FIG. 8A and FIG. 8B illustrate projections for SSMVEP BCI use with AR-OST 800 in accordance with one embodiment. The AR-OST BCI configuration 600 of FIG. 6 may be used to exercise a user's interaction with an AR-OST and BCI using the projections for SSMVEP BCI use with AR-OST 800.

In one embodiment, as shown in FIG. 8A, a monitor display 802 may comprise a non-active background 402 previously discussed, such as a black screen. The base SSMVEP pattern 302 may be shown as the AR-OST shield display 804. This base SSMVEP image 304 may be generated by a smart device in place within a smart device slot in the frame as described with respect to FIG. 6. The smart device may comprise an app designed to interact with the SSVEP BCI system or may be paired through a wired or wireless connection with an additional computing device configured to produce the base SSMVEP image 304 and its variations.

In an alternative embodiment illustrated in FIG. 8B, the monitor display 802 may comprise the active background 404 introduced with respect to FIG. 4B, and the base SSMVEP pattern 302 and its variations may again be shown as the AR-OST shield display 804.

While FIG. 8A and FIG. 8B illustrate a potential controlled laboratory setup for testing, FIG. 8C illustrates a real-world use-case for the projections for SSMVEP BCI use with AR-OST 800. A user 602 wearing an AR-OST 604 may be interacting out in the real world amid the user's environment 808, such as walking down a sidewalk along a city street. In this case, the user view through AR-OST shield 806 may incorporate the base SSMVEP pattern 302 as a digital graphical element mixed with a visual perception of the user's environment 808 by action of components integrated into or associated with the AR-OST 604 as disclosed herein.

Figure 9:
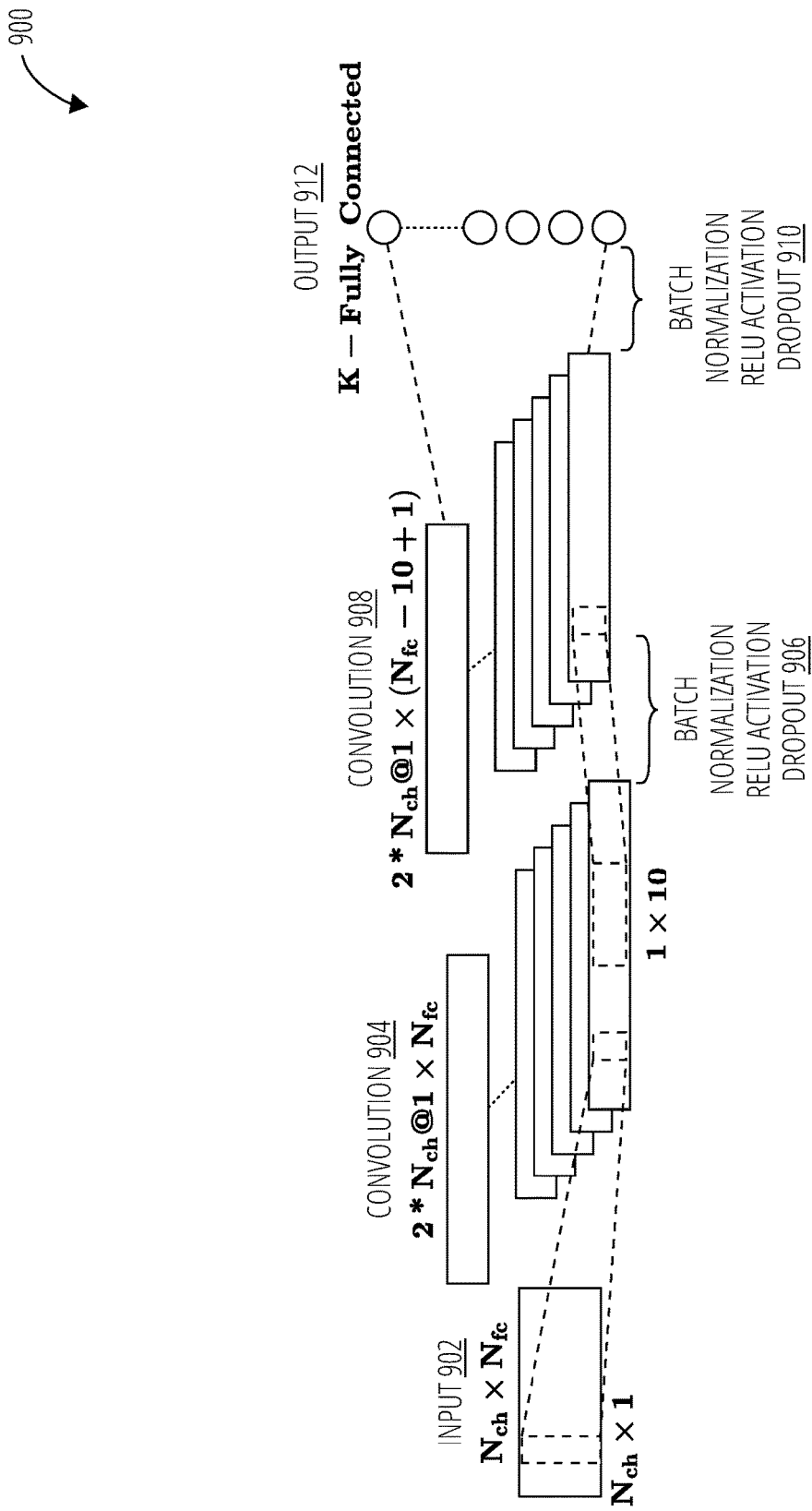
FIG. 9 illustrates a C-CNN process 900 in accordance with one embodiment.

FIG. 9 illustrates a C-CNN process 900 in accordance with one embodiment. The input 902 may be passed through convolution 904, and the results of convolution 904 may go through a batch normalization ReLU activation dropout 906 step. The data from the batch normalization ReLU activation dropout 906 may pass through convolution 908. The results of convolution 908 may undergo a batch normalization ReLU activation dropout 910 step, finally producing output 912 as shown. A C-CNN process 900 such as this may provide higher accuracy for asynchronously processed data than conventional approaches such as canonical correction analysis (CCA) and CNN using magnitude spectrum as input. The C-CNN method may be trained on both the SSVEP and SSMVEP data for stimulus detection.

The C-CNN process 900 may process BCI data in an asynchronous manner with a fixed window length (W=[1 second, 2 seconds]) and a step size of 0.1 seconds, in one embodiment. Window lengths greater than 2 seconds may considerably affect the speed of the overall BCI system when applied in real-time. The C-CNN may be based on the concatenation of the real and imaginary parts of the Fast Fourier Transform (FFT) signal provided as input to the C-CNN. In one embodiment, the complex FFT of the segmented EEG data may be calculated at a resolution of 0.2930 Hz. Next, the real and imaginary frequency components may be extracted along each channel and concatenated into a single feature vector as: $I=Re(X)\|Im(X)$. As a result, the feature vectors for each channel may be stacked one below the other to form the input matrix $I_{C-CNN}$ with dimensions $N_{ch} \times N_{fc}$, where $N_{ch}=3$ and $N_{fc}=220$.

$$I_{C-CNN} = \begin{cases} Re\{FFT(x_{O1})\}, & Im\{FFT(x_{O1})\} \\ Re\{FFT(x_{Oz})\}, & Im\{FFT(x_{Oz})\} \\ Re\{FFT(x_{O2})\}, & Im\{FFT(x_{O2})\} \end{cases}$$

The C-CNN process 900 may be trained in a user-dependent scenario, wherein the classifier is trained on data from a single participant and tested on the data of the same participant. The preprocessing step may be provided as a data augmentation strategy to increase the number of training examples to train the C-CNN. An eight-fold stratified cross-validation may be performed to evaluate the performance of the classifier such that there are no overlapping samples between the train and validation folds. This is equivalent to a leave one-trial out cross-validation. For W=1 second, each fold may include 1456 and 912 segments in the training and testing set, respectively. For W=2 seconds, there may be 1176 and 168 segments in the training and testing set, respectively. Furthermore, the C-CNN may be trained individually for a single participant for each stimulus type, background type, and window length. The total number of trainable parameters may be 5482.

In one embodiment, the C-CNN may be trained on a processor and memory system such as an Intel Core i5-7200 central processing unit (CPU) @ 2.50 GHz and 8 GB random access memory (RAM). The categorical cross-entropy loss may be used to train the network. The final parameters of the network may be chosen based on the values that provided the highest classification accuracy across participants. In one embodiment, the chosen parameters may be $\alpha=0.001$, momentum=0.9, D=0.25, L=0.0001, E=50, and B=64, where $\alpha$ is the learning rate, D is the dropout rate, L is the L2 regularization constant, E is the number of epochs, and B is the batch size, these parameters being well understood in the art.

In another embodiment, the classification process may be performed by a heuristic, expert-system, transformer, long short-term memory (LSTM), recurrent neural network (RNN), CCA or any other classification algorithm suitable for processing multiple time-dependent input signals into a pre-defined set of classes.

The offline decoding performance for an asynchronous four-class AR-SSVEP BCI under the non-active background and 1-second window length may be 82%±15% with the C-CNN method described herein. The AR-SSMVEP BCI may achieve offline decoding performances of non-active background (NB): 71.4%±22% and active background (AB): 63.5%±18% for W=1 s, 83.3%±27% (NB) and 74.1%±22% (AB) for W=2 s with the C-CNN method. The asynchronous pseudo-online SSMVEP BCI using the C-CNN approach may provide high decoding performance that may not need to be precisely synchronized to the onset of the stimulus. Additionally, this approach may be robust to changes in background conditions. A difference in the performance between the steady-state and transition state may be observed and may be attributed to the method of segmentation and training. As transition state windows may not be seen by the classifier during the training phase, these regions may be misclassified in the pseudo-online testing phase. Windows during transition states may contain a mixture of steady-state and transition state data, making it a challenge to label such windows. This scenario closely resembles the errors that may likely occur in an online system. One simple solution may be to increase the detection window length. This may reduce errors and enhance the overall performance.

Figure 10:
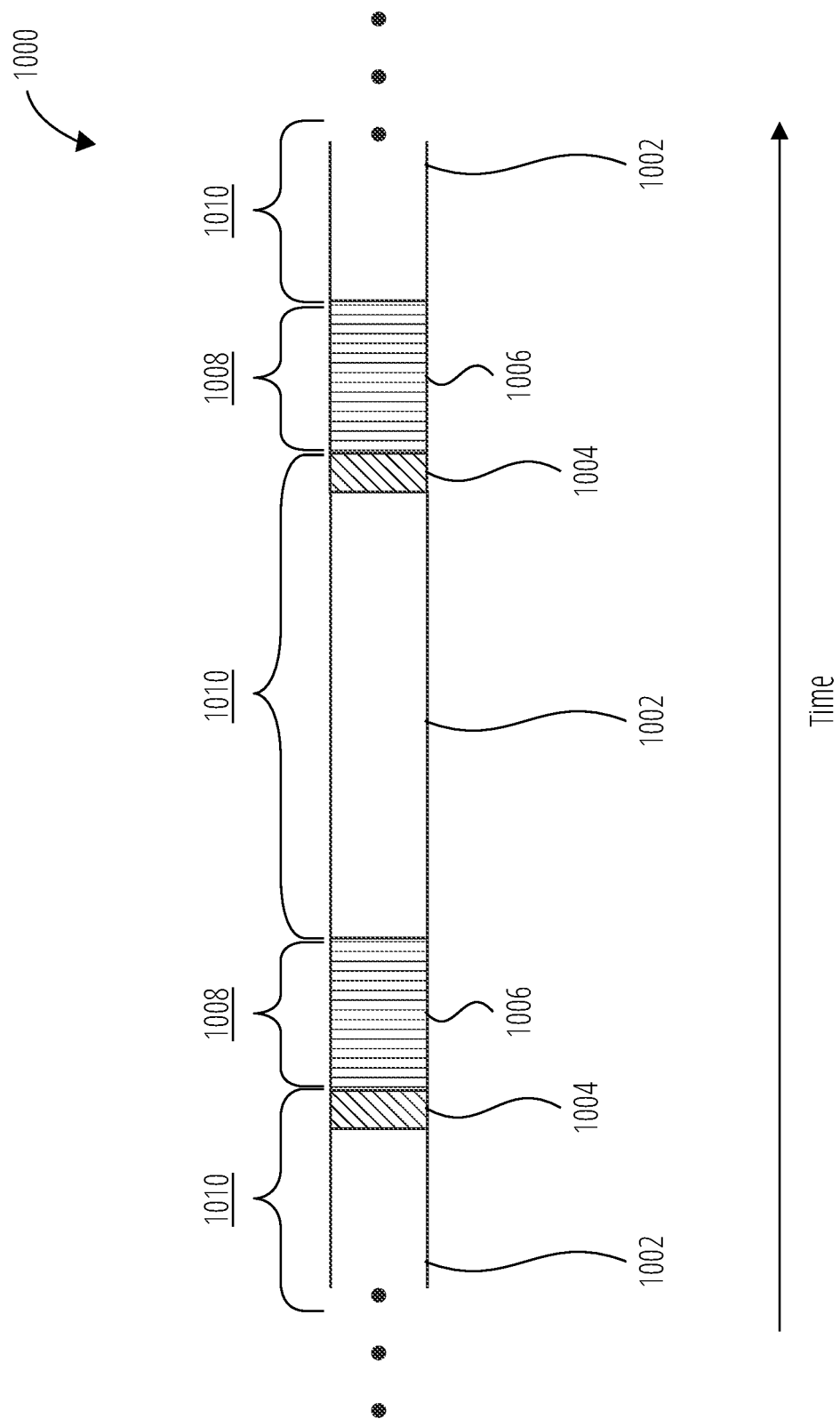
FIG. 10 illustrates IC states and NC states 1000 in accordance with one embodiment.

FIG. 10 illustrates IC states and NC states 1000 in accordance with one embodiment. A user's time wearing and interacting with an AR-OST and BCI may comprise break periods 1002, cue periods 1004, and stimulation periods 1006. In a training, calibration, or evaluation setting, these periods may be set as predetermined, fixed lengths of time. For example, a cue period 1004 of 2 seconds may precede a 6-second stimulation period 1006. During the cue period 1004, the stimulus to be focused on during the stimulation period 1006 may be highlighted. During the stimulation period 1006, that stimulus may be modulated at the desired frequency. A 4-second break period may ensue, during which no stimulus is presented.

During asynchronous interaction with the AR-OST and BCI, a wearer may have cue periods 1004 and stimulation periods 1006 with different timings, may have no cue period 1004 and may have break periods 1002 of no specific duration, with no established periodicity of stimulus presentation. Stimuli may rather be presented as circumstances arise in the user's environment, or as the user invokes certain use modes asynchronously.

In one embodiment, a BCI may assume that break periods 1002 and cue periods 1004 constitute NC states 1010. With no stimuli presented, no control may be intended by a user. When stimuli are presented during stimulation periods 1006, the BCI may assume that the user has entered an IC state 1008. As described with regard to decision block 112 of FIG. 1, other aspects of user interaction, such as gaze detection, may be monitored to determine that a user intends to control some aspect of their AR experience.

To refine the processing of EEG signals based on assumption or detection of an IC state 1008 versus an NC state 1010, the final softmax layer of the C-CNN architecture may be modified to include a fifth NC class. This may result in a total of five neurons: four IC=($C_1$, $C_2$, $C_3$, $C_4$) states and one NC=$C_5$ state. The convolutional layers and kernels may remain the same as in the four-class architecture. An 8-fold cross-validation scheme may be used to evaluate the IC versus NC detection. The network may be trained with the categorical cross-entropy loss. The final parameters of the network may be chosen in one embodiment as: α=0.001, momentum=0.9, D=0.25, L=0.0001, E=80, and B=40.

In one embodiment, a two-class classification result (IC versus NC) may be deduced from the results of the five-class C-CNN. The four target stimuli predictions may be combined into a single category IC class, and the rest state/NC may be the second class. From the confusion matrices, a true positive (TP) may be defined during the IC state when the user is looking at the target and the classifier predicts this segment correctly as an IC state. A false positive (FP) may be defined when the classifier predicts a segment as IC when the true label is the NC state. If the classifier misclassified an IC state as NC, this may be defined as a false negative (FN). The F1-score and false activation rate (FAR) may then be calculated as:

$$F1 = \frac{TP}{TP + .05*(FP + FN)}$$

For practical applications, classifying an IC/active state into a different active state may have a more negative effect than classifying it as an inactive class. Therefore, the FAR may be defined as the rate of misclassifications within the different IC states, i.e. misclassification between one IC state and another IC state. Consider $IC \in \mathbb{R}^{N_c-1 \times N_c+1}$ to be the resultant confusion matrix of the five-class classification, where $N_c=4$ is the number of IC states. After normalizing the IC by the number of test examples in each class, the FAR per class ($F_j$) may be defined as:

$$F_j = 1 - \frac{IC_{jj}}{\sum_{j=1}^{N_c} F_j}; j = \{1, 2, \ldots, N_c\}$$

Finally, the average FAR across all stimulus frequencies may be calculated according as:

$$FAR = \frac{1}{N_c}\sum_{j=1}^{N_c} F_j; j = \{1, 2, \ldots, N_c\}$$

The trained five-class C-CNN from one of the cross-validation folds may be applied in a pseudo-online manner on an entire training session. Specifically, this may be applied in a continuous decoding scenario which includes segments of data containing the transition segments between IC and NC. This step may emulate an online asynchronous BCI.

Figure 11A:
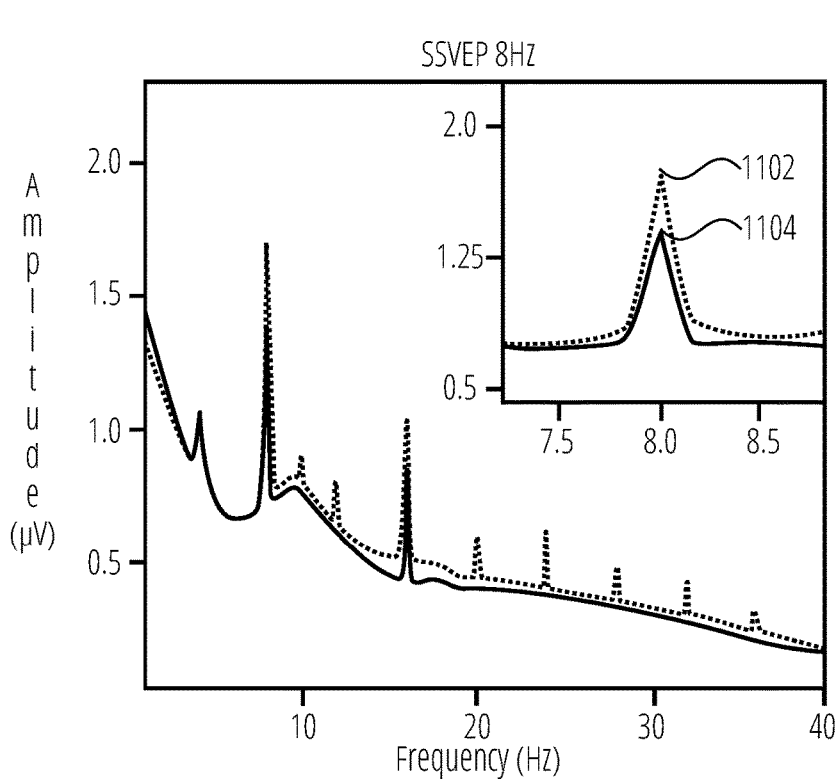
FIG. 11A-FIG. 11H illustrate the average magnitude spectrum of SSVEP and SSMVEP stimulus responses under non-active background and active background conditions.
Figure 11B:
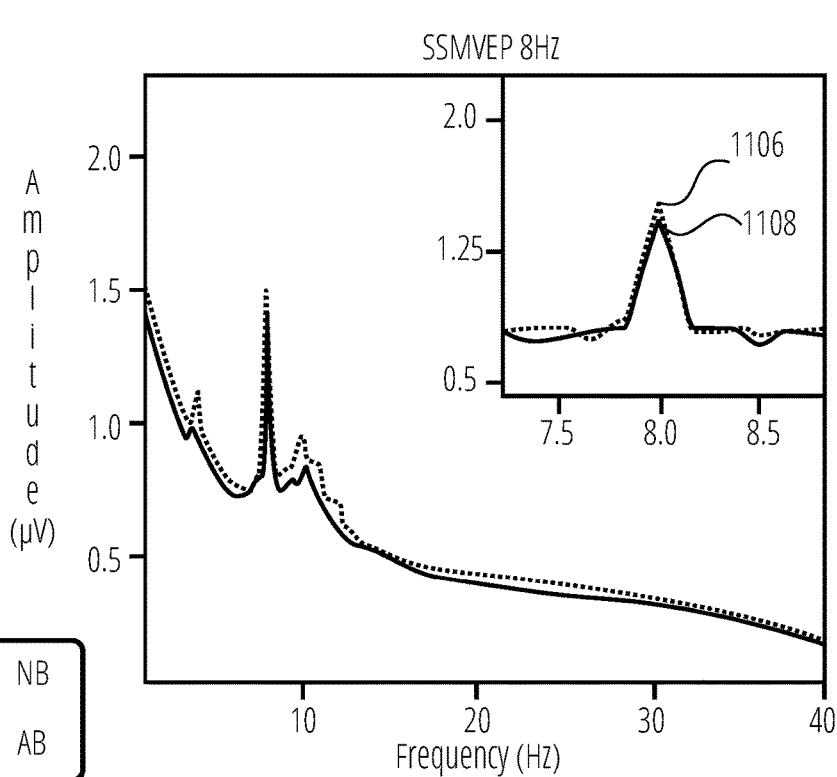
Figure 11C:
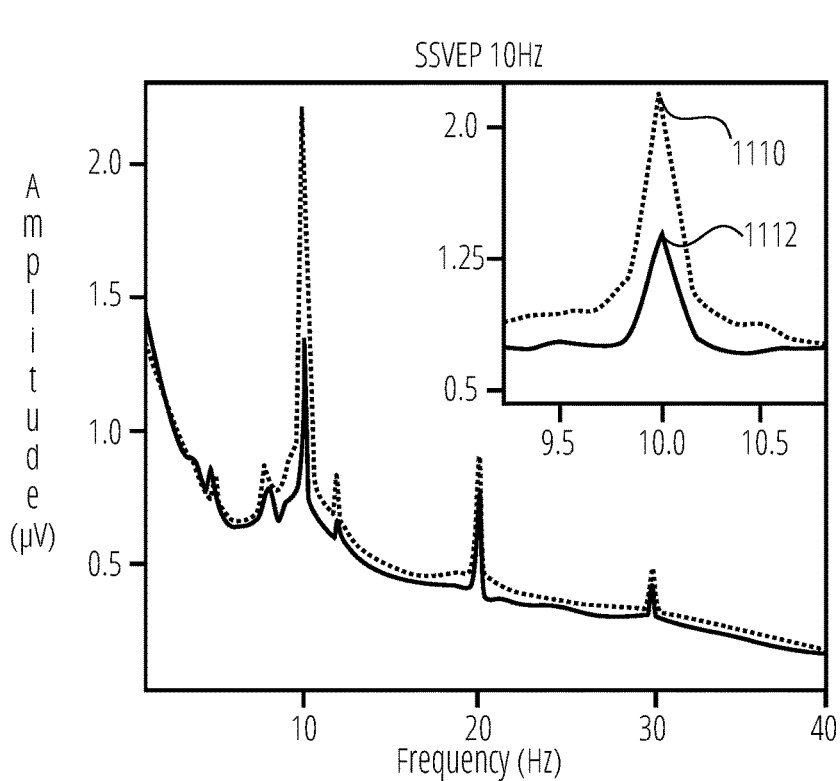
Figure 11D:
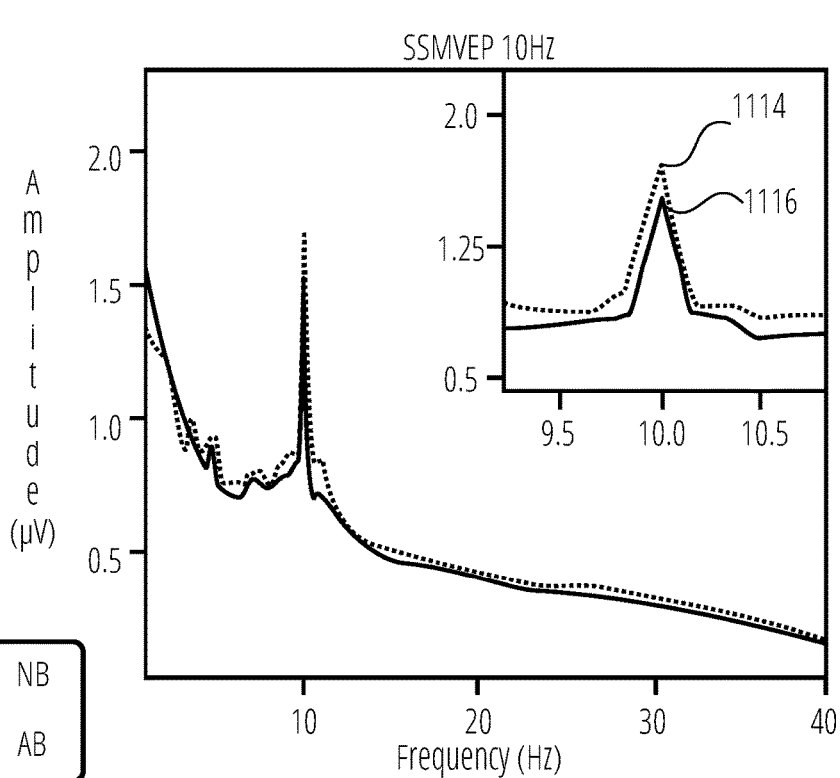
Figure 11E:
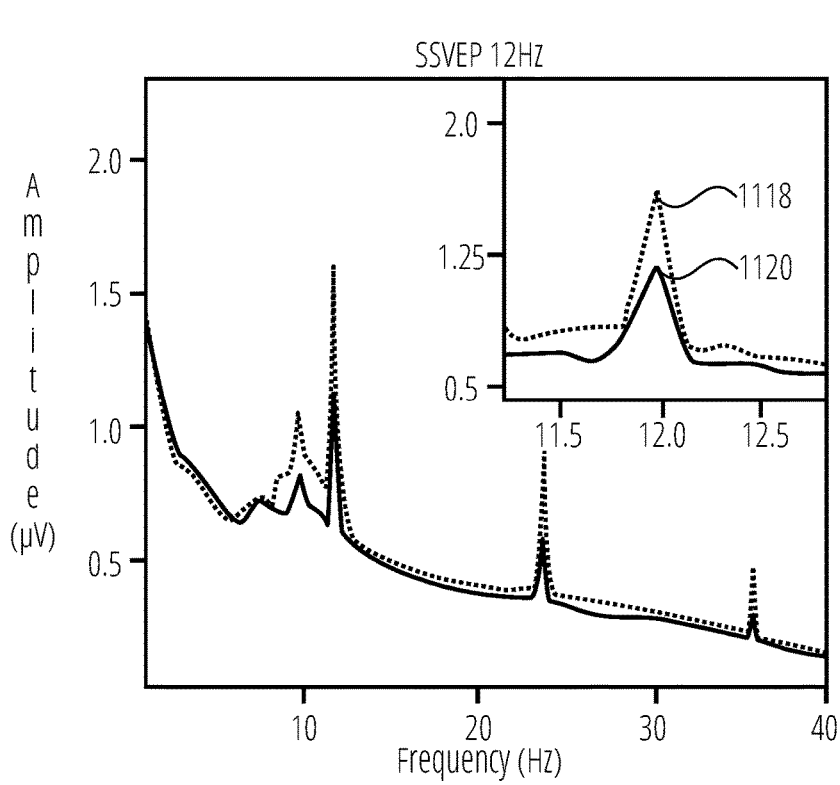
Figure 11F:
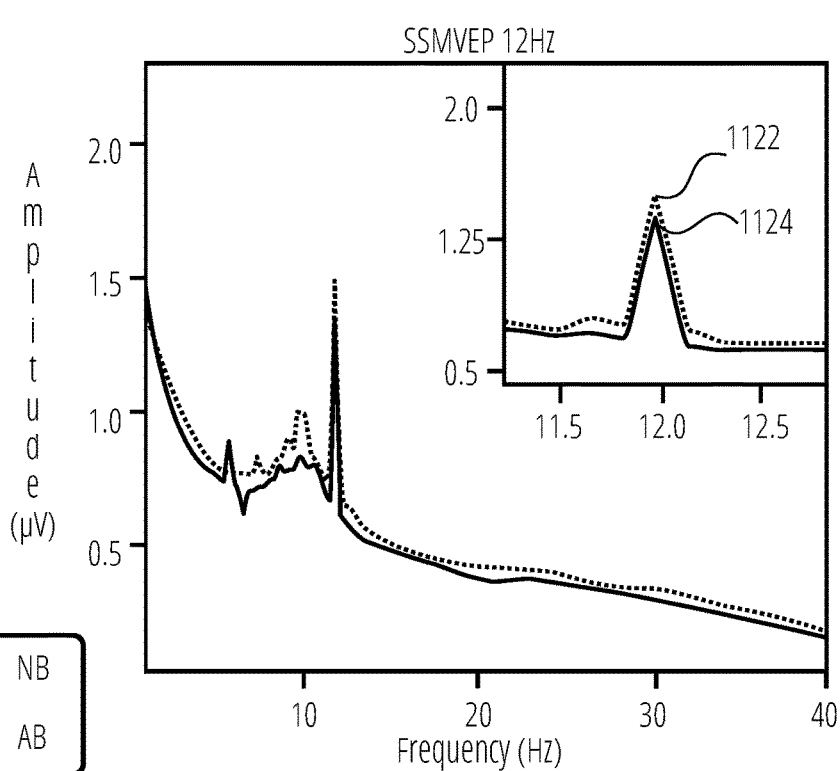
Figure 11G:
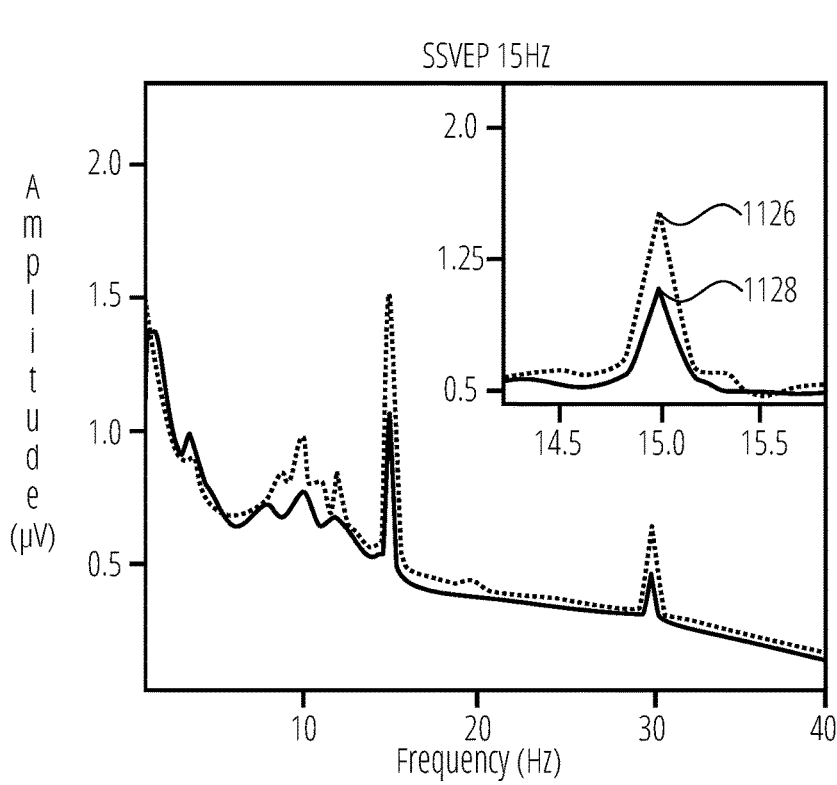
Figure 11H:
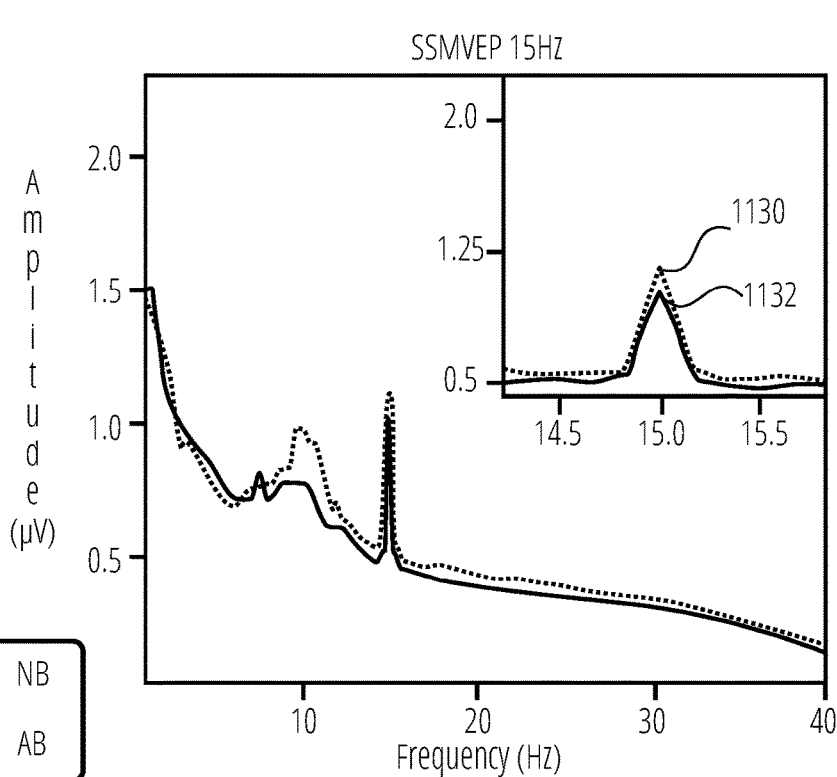

FIG. 11A-FIG. 11H FIG. 11A-FIG. 11H illustrate the average magnitude spectrum of SSVEP and SSMVEP stimulus responses under non-active background (NB) and active background (AB) conditions, as tested using an exemplary configuration. FIG. 11A illustrates SSVEP 8 Hz results 1100a. FIG. 11B illustrates SSMVEP 8 Hz results 1100b. FIG. 11C illustrates SSVEP 10 Hz results 1100c. FIG. 11D illustrates SSMVEP 10 Hz results 1100d. FIG. 11E illustrates SSVEP 12 Hz results 1100e. FIG. 11F illustrates SSMVEP 12 Hz results 1100f. FIG. 11G illustrates SSVEP 15 Hz results 1100g. FIG. 11H illustrates SSMVEP 15 Hz results 1100h.

The inserts in each graph show a magnified version of the fundamental stimulus frequencies. For the SSVEP 8 Hz results 1100a, NB peak response 1102 and AB peak response 1104 are shown. For the SSMVEP 8 Hz results 1100b, NB peak response 1106 and AB peak response 1108 are shown. For the SSVEP 10 Hz results 1100c, NB peak response 1110 and AB peak response 1112 are shown. For the SSMVEP 10 Hz results 1100d, NB peak response 1114 and AB peak response 1116 are shown. For the SSVEP 12 Hz results 1100e, NB peak response 1118 and AB peak response 1120 are shown. For the SSMVEP 12 Hz results 1100f, NB peak response 1122 and AB peak response 1124 are shown. For the SSVEP 15 Hz results 1100g, NB peak response 1126 and AB peak response 1128 are shown. For the SSMVEP 15 Hz results 1100h, NB peak response 1130 and AB peak response 1132 are shown.

Average magnitude spectra of the SSVEP and SSMVEP responses for the four stimulus frequencies (8 Hz, 10 Hz, 12 Hz, and 15 Hz) under the two background conditions (NB and AB) may be averaged across all participants, trials, and electrode channels (O1, Oz, O2) to achieve exemplary results such as those illustrated herein. The average magnitude spectrum for each SSVEP stimulus clearly indicate the peaks at the targeted fundamental stimulus frequency and its corresponding harmonics. Next, for each SSMVEP stimulus, a prominent peak at the targeted fundamental frequency may be observed for all frequencies, and no other prominent responses were observed at corresponding harmonics. These results confirm that the visual stimuli designed for the proposed optical see-through AR system may elicit the desired SSVEP and SSMVEP responses.

It may also be observed that the presence of an active background may reduce the amplitude of the response at the fundamental frequencies and harmonics for the SSVEP stimulus. The difference in the amplitudes computed between NB and AB for each stimulus frequency may be: 0.3 µV (8 Hz), 0.86 µV (10 Hz), 0.44 µV (12 Hz), and 0.43 µV (15 Hz), respectively, as indicated. On the other hand, for the SSMVEP stimulus, the difference in amplitudes of the fundamental frequencies between NB and AB may be: 0.05 µV (8 Hz), 0.19 µV (10 Hz), 0.13 µV (12 Hz) and 0.09 µV (15 Hz), respectively. The average reduction in amplitude from NB to AB for all stimulus frequencies may be: 28.2% and 8.3% for the SSVEP and SSMVEP responses, respectively. The average SNR across all participants for the SSVEP stimulus for NB versus. AB may be (dB): 6.75 versus 5.43 at 8 Hz, 8.15 versus 5.9 at 10 Hz, 6.9 versus 5.32 at 12 Hz, and 8.82 versus 6.7 at 15 Hz. On the contrary, the SNR values for the SSMVEP stimulus may be (dB): 5.65 versus 5.32 at 8 Hz, 6.59 versus 5.77 at 10 Hz, 6.11 versus 6.09 at 12 Hz, and 6.02 versus 6.17 at 15 Hz. The average reduction in SNR between NB and AB across all frequencies for SSVEP and SSMVEP were 1.75 dB and 0.25 dB, respectively.

For the SSVEP stimulus, active background may result in consistently lower CCA coefficients than the non-active background across all stimulus frequencies. In contrast, for the SSMVEP stimulus, the magnitude of the CCA coefficients may be similar between the two backgrounds across all stimulus frequencies. This may indicate that measured perception of the SSMVEP stimulus is less affected by the presence of the active background than measured perception of a similar SSVEP stimulus. For both stimulus types, the response to the 15 Hz stimulus may be most impacted by the presence of the active background.

One of the reasons for the reduction in the amplitude due to the active background may be attributed to the presence of competing stimuli in the background. Previous studies have shown that when multiple flickering visual stimuli are placed in the same visual field, they compete for neural representations. This is called the effect of competing stimuli. Therefore, it is possible that various visual elements in the background video may interfere with or compete for neural representations leading to the decrease in the overall robustness of the SSVEP stimulus. On the other hand, there may be no reduction in the magnitude of the response for SSMVEP stimuli when an active background is introduced. This may show that the SSMVEP stimulus is more robust even in the presence of competing stimuli in the background.

The reduction in the amplitude of the response for both stimulus types may be attributed to an increase in visual and mental load in the presence of an active background. Mental load induced by the flickering SSVEP stimulus may be higher than for the SSMVEP stimulus. The reduction in attentional demands by the SSMVEP stimulus in general may, therefore, lead to higher performance with SSMVEP stimuli compared to SSVEP stimuli.

Figure 12:
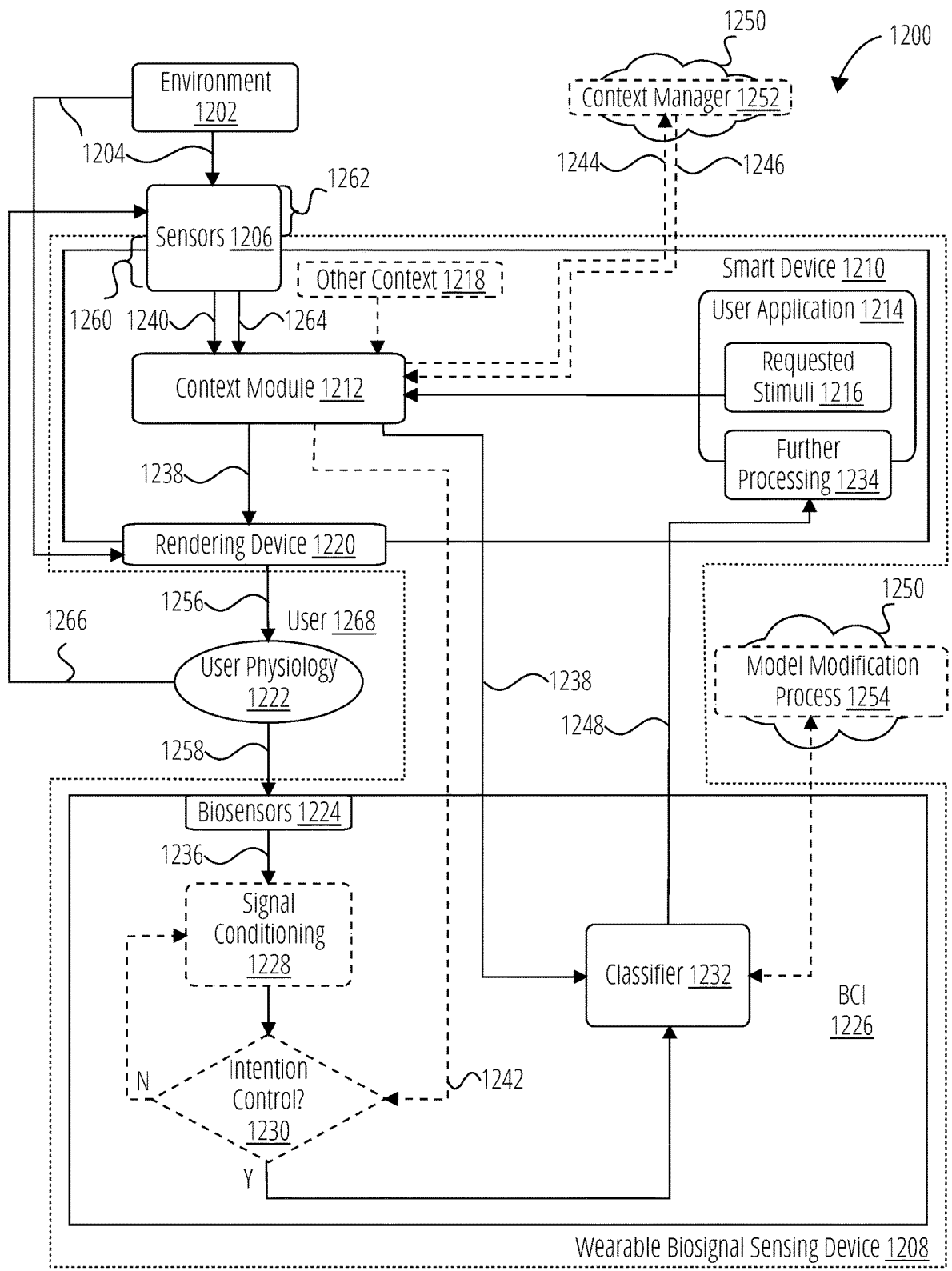
FIG. 12 illustrates a system 1200 in accordance with one embodiment.

FIG. 12 illustrates a system 1200 in accordance with one embodiment. The system 1200 may comprise sensors 1206 and a wearable biosignal sensing device 1208 worn by a user 1268, which may have integrated or be closely associated or paired with a smart device 1210 and a BCI 1226. The smart device 1210 may include a context module 1212, a user application 1214, and a rendering device 1220. The BCI 1226 may include biosensors 1224, signal conditioning 1228, intentional control signal detection 1230, and a classifier 1232. The system 1200 may in some embodiments include a context manager 1252 and model modification process 1254 stored on and accessed through connection to cloud server 1250.

The sensors 1206 may be integrated with either, both, or neither of the wearable biosignal sensing device 1208 and the smart device 1210. The sensors 1206 may also be worn by or mounted on equipment worn or carried by the user 1268. Sensors integrated into the wearable biosignal sensing device 1208 and smart device 1210 may be referred to herein as internal sensors 1260. Sensors not so integrated may be referred to herein as external sensors 1262.

In one embodiment, sensors 1206 may receive environmental stimulus 1204 from the surrounding environment 1202. These sensors 1206 may be internal sensors 1260 or external sensors 1262 that detect visual light, light beyond the visual spectrum, sound, pressure, temperature, proximity of objects in the environment, acceleration and direction of motion of objects in the environment or of the wearable biosignal sensing device 1208 and user 1268, or other aspects of the environment 1202 and action within the environment 1202, as is well understood in the art.

In one embodiment, sensors 1206 may also detect information about a user's physical state and actions 1266. For example, the sensors 1206 may be external sensors 1262 that are body-mounted sensors such as cameras, heart-rate monitors, ambulatory medical devices, etc. These sensors 1206 may detect aspects of the user's action, movements, intents, and condition through, e.g., gaze detection, voice detection and recognition, perspiration detection and composition, etc., as is well understood in the art. The sensors 1206 may provide output as sensor data 1264. The sensor data 1264 may carry information associated with environmental stimulus 1204 and user's physical state and actions 1266 as detected by the internal sensors 1260 and external sensors 1262 that make up the sensors 1206.

In some embodiments it may be useful to differentiate environmental stimuli data 1240 from the other sensor data 1264, and environmental stimuli data 1240 may be sent as part of a separate data signal stream and may undergo additional or alternative logical analysis, processing, and use as needed. In other embodiments, all components of the sensor data 1264, including environmental data generated in response to environmental stimuli 1204, may be undifferentiated in this regard, and may be considered as part of a single data signal stream.

The wearable biosignal sensing device 1208 may be a physical assembly that may include sensors 1206, a smart device 1210, and a BCI 1226. In one embodiment, the wearable biosignal sensing device 1208 may be an AR-OST 604 such as is described with respect to FIG. 6. The smart device 1210 may incorporate sensing, display, and network functions. The smart device 1210 may in one embodiment be a smartphone or small tablet computer that may be held within a smart device slot 610 of an AR-OST 604. In one embodiment, the smart device 1210 may be an embedded computer such as a Raspberry Pi single board computer. In one embodiment, the smart device 1210 may be a system on a chip (SoC) such as the Qualcomm SnapDragon SoC. In some embodiments, the smart device 1210 may have an operating system such as Android or iOS configured to manage hardware resources and the life-cycle of user applications.

The smart device 1210 may be further configured with at least one user application 1214 in communication with the context module 1212 for the purpose of augmenting user interaction with the user application 1214 to include AR handsfree control through the interaction of the sensors 1206, the wearable biosignal sensing device 1208, user physiology 1222, and the BCI 1226. User applications 1214 may be applications executed on the smart device that rely upon user interaction. Such user applications 1214 may include virtual input devices such as a virtual keyboard, heads-up interactive map interfaces, such as Google Maps and Waze, virtual assistants, such as Amazon's Alexa or Apple's Siri, etc.

In one embodiment, other context data 1218 may be available to the solution disclosed herein. Other context data 1218 may include data that is un-sensed, i.e., data obtained, not from sensors 1206, but through interaction of the smart device 1210 with the Internet and with user applications 1214 operating on the smart device 1210. For example, other context data 1218 may include a date and time of day detected from a smart device's built-in timekeeping capabilities or obtained from the Internet, an appointment from a calendar application, including a specific location and time of the appointment, application notifications and messages, etc.

The context module 1212 may be a standalone application or may be compiled within other commercially available applications and configured to support the solution disclosed herein. The context module 1212 may receive any combination of environmental stimuli data 1240, sensor data 1264, and other context data 1218 from the sensors 1206 (either or both internal sensors 1260 and external sensors 1262) and the smart device 1210. The data provided to the context module 1212 may comprise at least one of environmental stimuli data 1240, sensor data 1264, other context data 1218. In one embodiment, the data provided to the context module 1212 includes environmental stimuli data 1240. In one embodiment, the data provided to the context module 1212 includes sensor data 1264. In one embodiment, the data provided to the context module 1212 includes other context data 1218. In one embodiment, the data provided to the context module 1212 includes environmental stimuli data 1240 and sensor data 1264. In one embodiment, the data provided to the context module 1212 includes environmental stimuli data 1240 and other context data 1218. In one embodiment, the data provided to the context module 1212 includes sensor data 1264 and other context data 1218. In one embodiment, the data provided to the context module 1212 includes environmental stimuli data 1240, sensor data 1264, and other context data 1218. The environmental stimuli data 1240, sensor data 1264, and other context data 1218 may include at least one of environmental data, body-mounted sensor data, connected ambulatory device data, location specific connected device data, and network connected device data.

The context module 1212 may receive one or more requested stimuli data 1216 from a user application 1214 on the smart device 1210. These requested stimuli data 1216 may indicate that the user application 1214 needs a user to select from among a number of options. The context module 1212 may include a process for determining device context state from the receipt of at least one of environmental stimuli data 1240, sensor data 1264, and other context data 1218, from internal sensors 1260 implemented on the wearable biosignal sensing device 1208 or the smart device 1210, external sensors 1262 in communication with the smart device 1210 or wearable biosignal sensing device 1208, or un-sensed data included in other context data 1218.

The context module 1212 may further incorporate the ability to transform at least a portion of the requested stimuli data 1216 from a user application 1214 into modified stimuli 1238 based at least in part on the environmental stimuli data 1240, sensor data 1264, and other context data 1218 that inform the device context state. The context module 1212 may in this manner develop modified stimuli 1238 which may be provided to a user 1268 of the wearable biosignal sensing device 1208 in order to allow the user 1268 to make a selection among the options indicated by the requested stimuli data 1216 using a BCI-enabled AR interface. The modified stimuli 1238 may incorporate visual icons, such as the SSMVEP stimuli introduced with respect to FIG. 3A. These SSMVEP stimuli may be modified by the context module 1212 based on a device context state, e.g., to improve distinctions between the options presented to the user and the environmental stimuli 1204 they may compete with to gain user attention. Thus the context module 1212 may use the context provided by environmental stimuli data 1240, sensor data 1264, and other context data 1218 to create modified stimuli 1238 that may evoke more easily distinguished responses from a user 1268 through the wearable biosignal sensing device 1208 and BCI 1226 than the default SSMVEP stimuli, other default stimuli, and requested stimuli data 1216 may be able to accomplish unmodified.

For example, if environmental stimuli 1204 are detected as environmental stimuli data 1240 that exhibit a periodic behavior at a 10 Hz frequency, rather than use a default generated stimulus exhibiting behavior at 10 Hz, the context module 1212 may transform that 10 Hz default generated stimulus to exhibit its behavior at a frequency of 12 Hz, such that user attention on the environmental stimulus exhibiting 10 Hz behavior is not mistaken for the user 1268 fixating on a menu option behaving at a similar frequency. Modifications based on environmental stimuli 1204 may also include changing where a stimulus presented for user selection is located in the user's field of vision, transforming the evoked potential to an auditory or haptic stimulus response, or other modifications rendered expedient by the environmental conditions detected through the environmental stimuli data 1240, or as specified by user preferences available through smart device 1210 configuration.

The smart device 1210 may incorporate a passive or active rendering device 1220 capability. This may allow the modified stimuli 1238 as well as environmental stimuli 1204 to be presented to the user 1268. This rendering device 1220 may mix environmental stimuli 1204 with modified stimuli 1238, resulting in rendered stimuli 1256 for presentation to the user's sensory system, allowing the user 1268 to perceive both conditions of the environment 1202 and selections integral to operating a user interface of a user application 1214. The modified stimuli and environmental stimuli 1204 may be rendered using at least one of a visual device, an auditory device, and a haptic device sensed by the user 1268. In one embodiment, the rendering device 1220 capability may be provided by a transparent, partially reflective AR-OST shield 606, as described with respect to FIG. 6. Environmental stimuli 1204 may be directly perceived by a user, visual stimuli being carried through light transmitted through the AR-OST shield 606. Visual aspects of modified stimuli 1238 may be rendered for display, displayed on the smart device 1210 residing in the smart device slot 610, and reflected back to a user's eyes due to the partially reflective properties of the AR-OST shield 606 material. In another embodiment, the wearable biosignal sensing device 1208 may incorporate an opaque headset and may rely on sensing and presentation hardware such as cameras and video projections to provide environmental stimuli 1204 mixed with modified stimuli 1238 as rendered stimuli 1256 to the user. In another embodiment, the wearable biosignal sensing device 1208 may incorporate a transparent OLED display to enable optical pass-through and rendering of modified stimuli 1256.

The rendered stimuli 1256 presented to the user 1268 may generate a response through user physiology 1222. User physiology 1222 may refer to a user's body and associated peripheral and central nervous system. Human responses to visual, auditory, haptic, or other stimuli, as expressed by bodily and especially nervous system reactions, are well understood in the art, and may be detected using biosensors 1224. Biosensors 1224 may be a plurality of sensors mounted on the user 1268 body and/or incorporated into the BCI 1226 that detect nervous system activity. These biosensors 1224 may be EEG electrodes 618, electromyography (EMG) electrodes, electrocardiography (EKG) electrodes, other cardiovascular and respiratory monitors, blood oxygen level and glucose level monitors, and other biosensors 1224, as are well understood in the art.

Biosensors 1224 may provide biosignals 1236, as output. Biosignals 1236 are the raw signals recorded by biosensors 1224. The biosignals 1236 may be received from the biosensors 1224 and may be generated at least partially in response to the rendered stimuli 1256. The biosignals 1236 may be received on the wearable biosignal sensing device 1208. In some embodiments, the biosignals 1236 may undergo signal conditioning 1228. Signal conditioning 1228 may incorporate methods for filtering and cleaning raw data in the form of biosignals 1236. Such data may be filtered to omit noise, may undergo Fast Fourier Transform to detect energy at discrete frequency levels, may have statistical analyses applied such as detrending, or may be processed through other digital signal processing algorithms as are well known in the art. In some embodiments, a classifier 1232 of the BCI 1226 may be able to accept raw biosignals 1236 without need for signal conditioning 1228.

In some embodiments, the BCI 1226 may incorporate intentional control signal detection 1230. This may be similar to the process described with respect to decision block 112 of FIG. 1. Intentional control signal detection 1230 may be a method for determining if the user is intending to fixate on one or more modified stimuli 1238. In one embodiment, the intentional control signal detection 1230 may determine the existence of an intentional control signal by determining, at least in part, from received biosignals 1236 that the user 1268 is intending to fixate on at least one of the rendered stimuli 1256. In another embodiment, the context module 1212 of the smart device 1210 may send a manual intention override 1242 signal to intentional control signal detection 1230, indicating that the intentional control signal detection 1230 may assume user intention control is present, regardless of the biosignals 1236 received.

In the absence of an intentional control signal, embodiments employing intentional control signal detection 1230 may continue to monitor for intentional control based on raw or conditioned biosignals 1236 and input from the context module 1212, without sending raw or conditioned biosignals 1236 to the classifier 1232. When an intentional control signal is detected, the intentional control signal detection 1230 may send the raw or conditioned biosignals 1236 to the classifier 1232. In some embodiments, intentional control signal detection 1230 may not be used, and raw or conditioned biosignals 1236 may be sent directly to the classifier 1232 from the biosensors 1224 or signal conditioning 1228, respectively.

The classifier 1232 may receive raw or conditioned biosignals 1236. The classifier 1232 may also receive the modified stimuli 1238 from the context module 1212 in order to refine classification through an understanding of expected user 1268 responses. The classifier 1232 may be configured to classify the received biosignals 1236 based on the modified stimuli 1238, resulting in a classified selection 1248. The classified selection 1248 may indicate which of the rendered stimuli 1256 the user is fixating on based on the modified stimuli 1238 and the biosignals 1236.

A classifier, as understood in the art, is an algorithm that maps input data to a specific category, such as a machine learning algorithm used to assign a class label to a data input. One example is an image recognition classifier that is trained to label an image based on objects that appear in the image, such as "person", "tree", "vehicle", etc. Types of classifiers include, for example, Perceptron, Naive Bayes, Decision Tree, Logistic Regression, K-Nearest Neighbor, Artificial Neural Networks, Deep Learning, and Support Vector Machine, as well as ensemble methods such as Random Forest, Bagging, and AdaBoost.

Traditional classification techniques use machine-learning algorithms to classify single-trial spatio-temporal activity matrices based on statistical properties of those matrices. These methods are based on two main components: a feature extraction mechanism for effective dimensionality reduction, and a classification algorithm. Typical classifiers use a sample data to learn a mapping rule by which other test data may be classified into one of two or more categories. Classifiers may be roughly divided to linear and non-linear methods. Non-linear classifiers, such as Neural Networks, Hidden Markov Model and k-nearest neighbor, may approximate a wide range of functions, allowing discrimination of complex data structures. While non-linear classifiers have the potential to capture complex discriminative functions, their complexity may also cause overfitting and carry heavy computational demands, making them less suitable for real-time applications.

Linear classifiers, on the other hand, are less complex and are thus more robust to data overfitting. Linear classifiers perform particularly well on data that may be linearly separated. Fisher Linear discriminant (FLD), linear Support Vector Machine (SVM) and Logistic Regression (LR) are examples of linear classifiers. FLD finds a linear combination of features that maps the data of two classes onto a separable projection axis. The criterion for separation is defined as the ratio of the distance between the classes mean to the variance within the classes. SVM finds a separating hyper-plane that maximizes the margin between the two classes. LR, as its name suggests, projects the data onto a logistic function.

Machine learning software may be custom computer code, may be commercially available for use in classification, or may be customized versions of commercially available machine learning. Examples of machine learning software include IBM Machine Learning, Google Cloud AI Platform, Azure Machine Learning, and Amazon Machine Learning.

The classifier 1232 may in some embodiments be implemented as a C-CNN, such as that introduced with respect to FIG. 9. A C-CNN, other neural network, or other machine learning algorithm may be trained to recognize patterns in raw or conditioned biosignals 1236 that correspond to a user's physiological response to the rendered stimuli 1256 that correspond to the modified stimuli 1238 associated with the requested stimuli data 1216. The classifier 1232 may classify a rendered stimulus 1256 as having user focus and may send this indication of focus as a classified selection 1248 for further processing 1234 by the smart device 1210, and in some embodiments specifically by the user application 1214 on the smart device 1210. Further processing 1234 may be processing occurring in the smart device 1210 and/or user application 1214 that analyzes and/or utilizes the classified selection 1248 from the classifier 1232.

In one embodiment, the smart device 1210 and BCI 1226 of the wearable biosignal sensing device 1208 may communicate with cloud server 1250, i.e., a network-connected computing resource. Cloud server 1250 may provide a connection to a context manager 1252 and model modification process 1254. The context manager 1252 may be a cloud-based system that provides additional context information via a network connection. The context module 1212 may send current device context state data and requests for other device context state data 1244 to the context manager 1252. The context module 1212 may in turn receive a response for recommended device context state and notifications and data for new stimuli 1246 from the context manager 1252.

A model modification process 1254 may also be available through cloud server 1250. The model modification process 1254 may act offline, i.e., asynchronously and apart from the activity of the components of the wearable biosignal sensing device 1208, smart device 1210, and BCI 1226. The model modification process 1254 may be a service that provides non-real-time updates to the classifier 1232, at times when the wearable biosignal sensing device 1208 is not in use, for example. One embodiment of use of the model modification process 1254 is described in greater detail with respect to FIG. 13.

Figure 13:
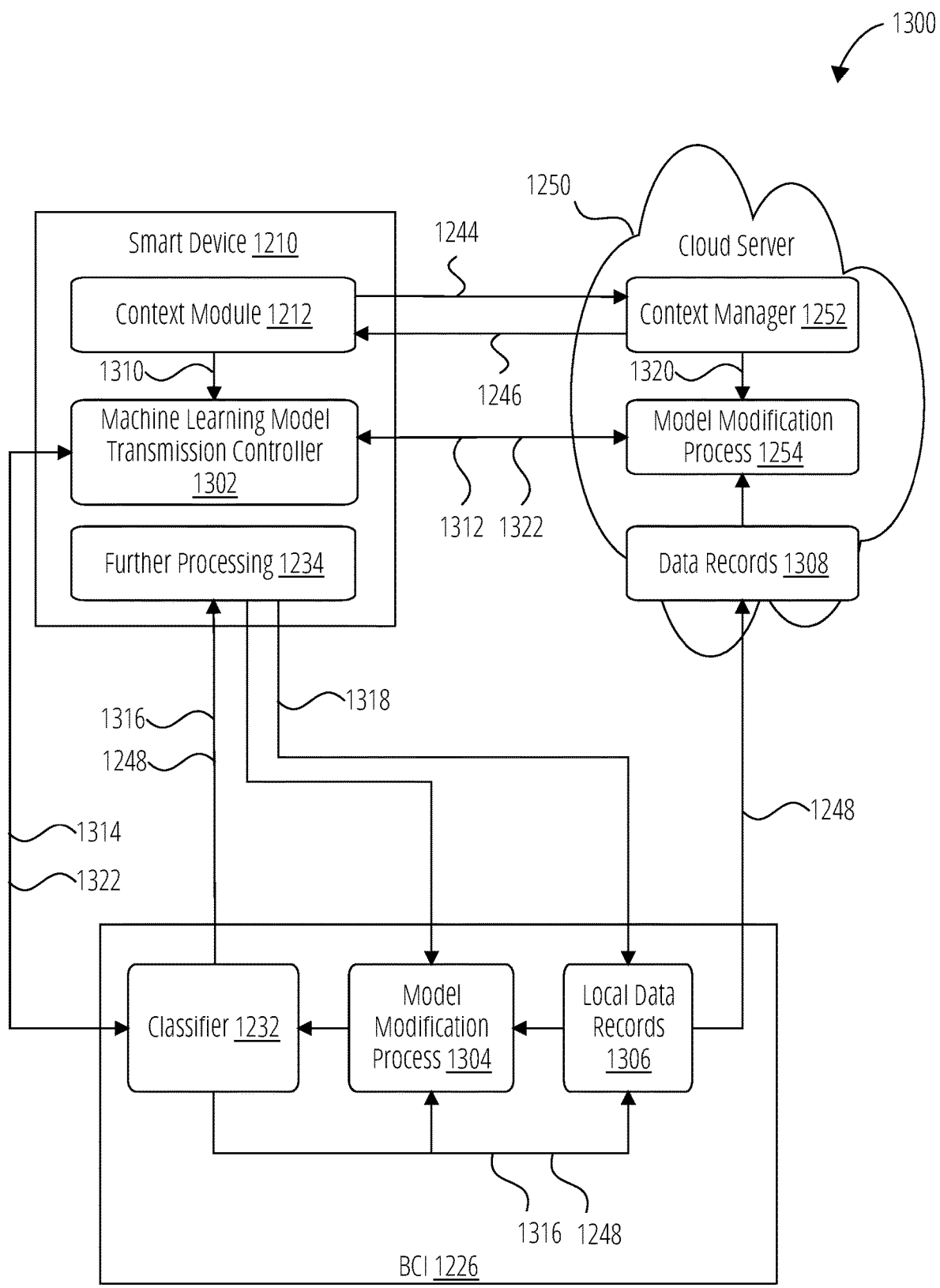
FIG. 13 illustrates classifier model modification 1300 in accordance with one embodiment.

FIG. 13 illustrates classifier model modification 1300 in accordance with one embodiment. In the system disclosed, "model modification" is defined as any parameter tuning, hyperparameter optimization, reinforcement learning, model training, cross-validation, or feature engineering methods that may be used to facilitate the classification of biosignal data. Classifier model modification 1300 may involve the elements of the system 1200 as illustrated, in addition to a machine learning model transmission controller 1302 implemented in the smart device 1210 along with the context module 1212, model modification process 1304 capabilities incorporated into the BCI 1226, as well as the model modification process 1254 in cloud server 1250, local data records 1306 stored on the BCI 1226, and data records 1308 stored in cloud server 1250. Elements of system 1200 not illustrated in FIG. 13 are omitted for simplicity of illustration but may be comprised in system 1200 embodiments configured to implement classifier model modification 1300.

As described with respect to FIG. 12, the context module 1212 may send current device context state data and requests for other device context state data 1244 to the context manager 1252 in cloud server 1250. The context module 1212 may in turn receive a response for recommended device context state and notifications and data for new stimuli 1246 from the context manager 1252. The context manager 1252 may send new state data and updated state data 1320 to the model modification process 1254 on the cloud server 1250 to be used in classifier model modification 1300. The cloud server 1250 may further receive the classified selection 1248 from the classifier 1232, either directly from elements on the BCI 1226 or through the further processing 1234 performed on the smart device 1210, to be used in classifier model modification 1300. The machine learning model 1314 may be updated using the at least one model modification process 1254 and at least one of the classified selection 1248 and the new state data and updated state data 1320.

The cloud server 1250 may send an updated or new machine learning model to the smart device (as shown by new machine learning models and updated machine learning models 1322). The updated machine learning model may be transmitted to the classifier using the machine learning model transmission controller 1302 on the smart device. In one embodiment, the context module 1212 on the smart device 1210 may request a new machine learning model from the cloud server 1250 using the machine learning model transmission controller 1302 (see request for new model 1310). The smart device 1210 may receive the new machine learning model from the cloud server 1250 (see new machine learning models and updated machine learning models 1322) and may transmit the new machine learning model to the classifier 1232.

In one embodiment, the context module 1212 of the smart device 1210 may send request for new model 1310 to a machine learning model transmission controller 1302. The machine learning model transmission controller 1302 may request and receive model specifications and initial parameters 1312 from the model modification process 1254 in cloud server 1250. The machine learning model transmission controller 1302 may then send a machine learning model 1314 to the classifier 1232 for use in classifying biosignals 1236 received by the classifier 1232 as described previously. The classifier 1232 may send predicted stimuli selected and associated metrics 1316 for further processing 1234.

In one embodiment, data from the further processing 1234 may be sent to a model modification process 1304 module on the BCI 1226, allowing the BCI 1226 to improve classification performed by the classifier 1232. In one embodiment, the classifier 1232 may send a more refined or optimized model developed through action of the model modification process 1304 back to the machine learning model transmission controller 1302, which may, in turn, provide that updated model to the model modification process 1254 in cloud server 1250.

In one embodiment, biosignal data and model parameters 1318 from further processing 1234 may be sent to local data records 1306 on the BCI 1226 for use in the model modification process 1304 located within the BCI 1226. The local data records 1306 may also be sent to the data records 1308 in cloud server 1250 for off-device storage. The data records 1308 may be available to the model modification process 1254 for offline classifier model modification 1300, to be performed independently from and asynchronously with the smart device 1210 and/or BCI 1226 of the wearable biosignal sensing device 1208.

Figure 14:
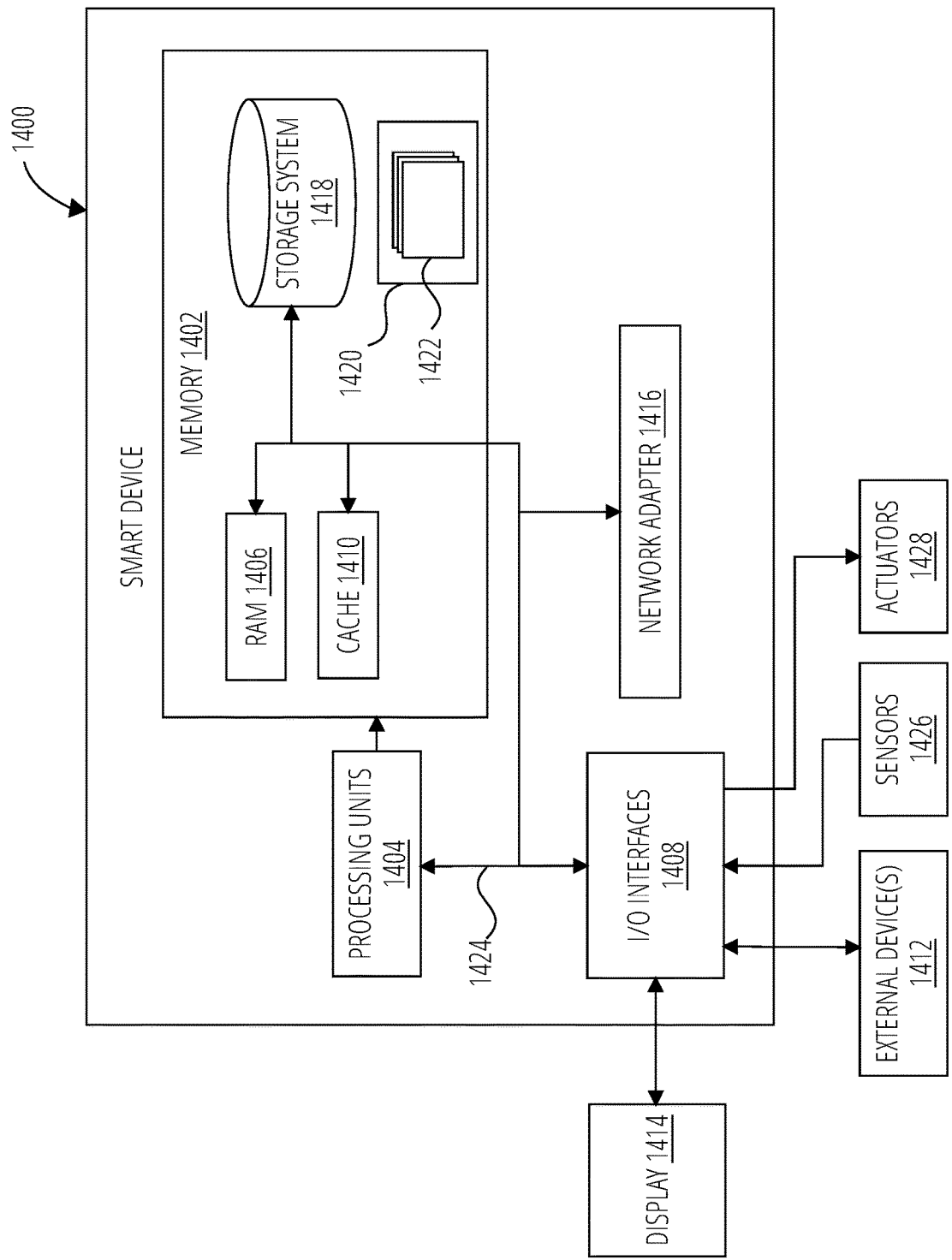
FIG. 14 illustrates a smart device 1400 in accordance with one embodiment.

As shown in FIG. 14, a smart device 1400 is shown in the form of a general-purpose computing device. The components of smart device 1400 may include, but are not limited to, one or more processors or processing units 1404, a system memory 1402, and a bus 1424 that couples various system components including system memory 1402 to processor processing units 1404. Smart device 1400 may include sensors 1426 such as cameras, accelerometers, microphones, etc., and actuators 1428, such as speakers, vibrating or haptic actuators, etc. Smart device 1400 may be a smartphone, a tablet, or other computing device suitable for implementing the disclosed solution as described herein.

Bus 1424 represents one or more of any of several types of bus structures, including a memory bus or memory controller, a peripheral bus, an accelerated graphics port, and a processor or local bus using any of a variety of bus architectures. By way of example, and not limitation, such architectures include Inter-Integrated Circuit (I2C), Serial Peripheral Interface (SPI), Controller Area Network (CAN), Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Smart device 1400 typically includes a variety of computer system readable media. Such media may be any available media that is accessible by smart device 1400, and it includes both volatile and non-volatile media, removable and non-removable media.

System memory 1402 may include computer system readable media in the form of volatile memory, such as Random access memory (RAM) 1406 and/or cache memory 1410. Smart device 1400 may further include other removable/non-removable, volatile/non-volatile computer system storage media. By way of example, a storage system 1418 may be provided for reading from and writing to a non-removable, non-volatile magnetic media (not shown and typically called a "hard drive"). Although not shown, a flash drive, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM, or other optical media, may be provided. In such instances, each may be connected to bus 1424 by one or more data media interfaces. As will be further depicted and described below, system memory 1402 may include at least one program product having a set (e.g., at least one) of program modules that are configured to carry out the functions of the disclosed solution.

Program/utility 1420 having a set (at least one) of program modules 1422 may be stored in system memory 1402 by way of example, and not limitation, as well as an operating system, one or more application programs, other program modules, and program data. Each of the operating system, one or more application programs, other program modules, and program data or some combination thereof, may include an implementation of a networking environment. Program modules 1422 generally carry out the functions and/or methodologies of the disclosed solution as described herein.

Smart device 1400 may also communicate with one or more external devices 1412 such as a keyboard, a pointing device, a display 1414, etc.; one or more devices that enable a user to interact with smart device 1400; and/or any devices (e.g., network card, modem, etc.) that enable smart device 1400 to communicate with one or more other computing devices. Such communication may occur via I/O interfaces 1408. I/O interfaces 1408 may also manage input from smart device 1400 sensors 1426, as well as output to actuators 1428. Still yet, smart device 1400 may communicate with one or more networks such as a local area network (LAN), a general wide area network (WAN), and/or a public network (e.g., the Internet) via network adapter 1416. As depicted, network adapter 1416 communicates with the other components of smart device 1400 via bus 1424. It will be understood by those skilled in the art that although not shown, other hardware and/or software components could be used in conjunction with smart device 1400. Examples include, but are not limited to: microcode, device drivers, redundant processing units, external disk drive arrays, redundant array of independent disks (RAID) systems, tape drives, data archival storage systems, etc.

Figure 15:
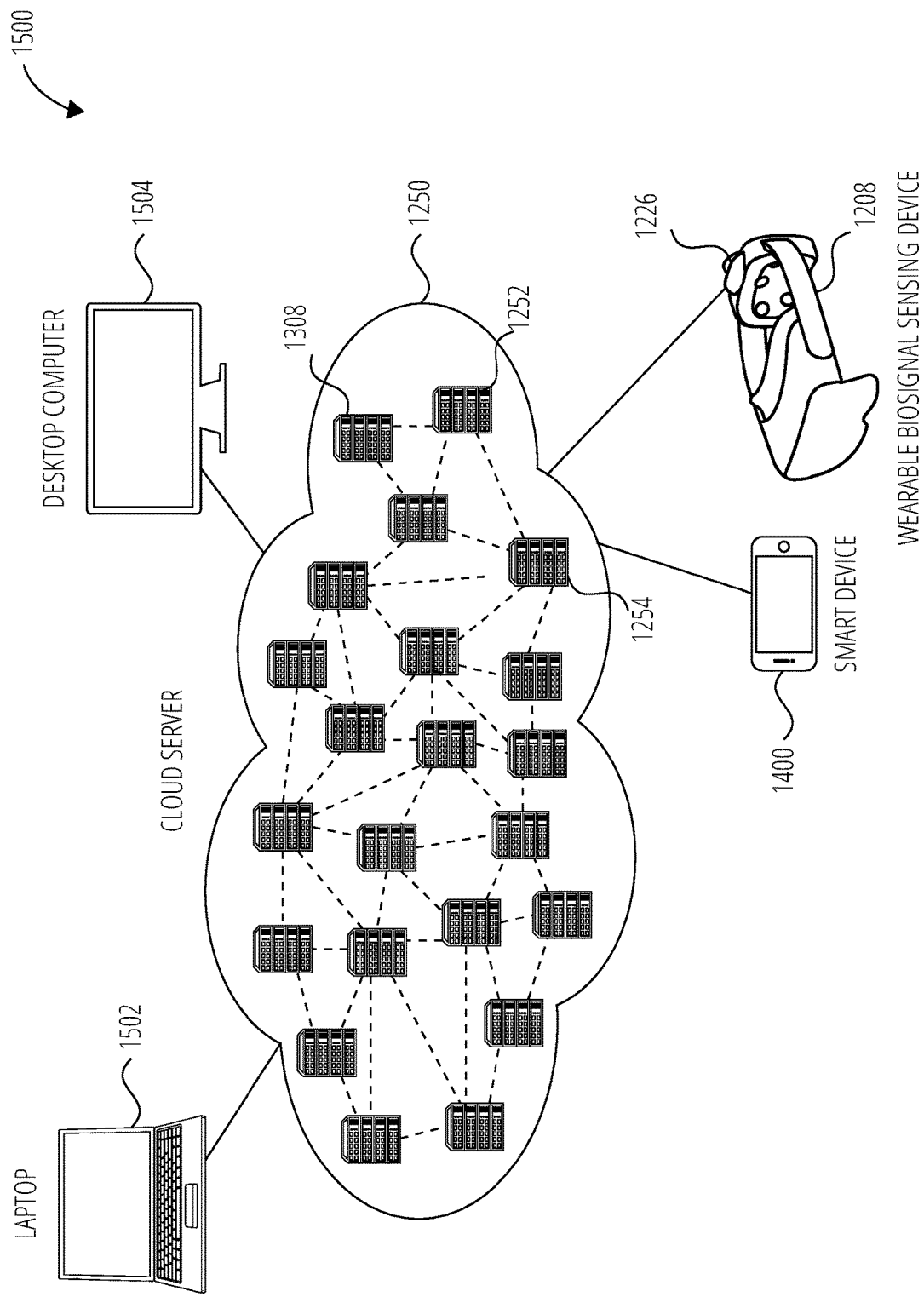
FIG. 15 illustrates a cloud computing system 1500 in accordance with one embodiment.

Referring now to FIG. 15, illustrative cloud computing system 1500 is depicted. "Cloud computing" refers to a model for enabling convenient, on-demand network access to a shared pool of configurable computing resources (e.g., networks, servers, storage, applications, and services) that may be rapidly provisioned and released with minimal management effort or service provider interaction. This cloud model promotes availability and is comprised of at least five characteristics, at least three service models, and at least four deployment models. Examples of commercially hosted cloud computing systems 1500 include Amazon Web Services (AWS), Google Cloud, Microsoft Azure, etc.

As shown, cloud computing system 1500 may comprise one or more cloud servers, including the context manager 1252, model modification process 1254, and data records 1308 previously described, with which computing devices such as, for example, personal digital assistant (PDA) or smart devices 1400, desktop computers 1504, laptops 1502, and/or wearable biosignal sensing device 1208 BCIs 1226 may communicate. This allows for infrastructure, platforms, and/or software to be offered as services (as described above in FIG. 14) from cloud server 1250, so as to not require each client to separately maintain such resources. It is understood that the types of computing devices shown in FIG. 15 are intended to be merely illustrative and that cloud server 1250 may communicate with any type of computerized device over any type of network and/or network/addressable connection (e.g., using a web browser).

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that may be rapidly provisioned and released with minimal management effort or interaction with a provider of the service. This cloud model may include at least five characteristics, at least three service models, and at least four deployment models.

Characteristics are as follows:

On-demand self-service: a cloud consumer may unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities may be rapidly and elastically provisioned, in some cases automatically, to quickly scale out and rapidly released to quickly scale in. To the consumer, the capabilities available for provisioning often appear to be unlimited and may be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage may be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which may include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 16:
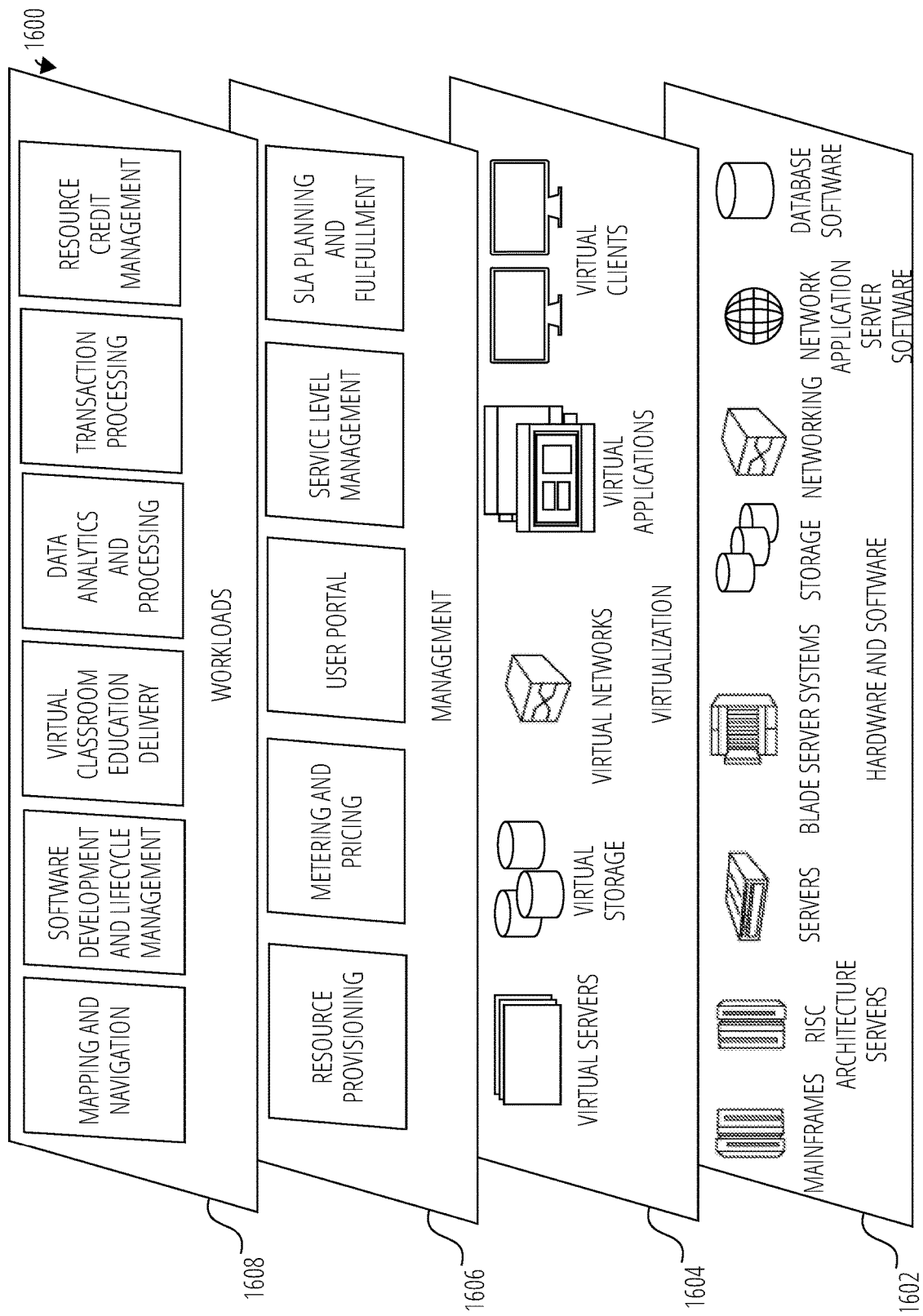
FIG. 16 illustrates cloud computing functional abstraction layers 1600 in accordance with one embodiment.

Referring now to FIG. 16, a set of cloud computing functional abstraction layers 1600 provided by cloud computing systems 1500 such as those illustrated in FIG. 15 is shown. It will be understood in by those skilled in the art that the components, layers, and functions shown in FIG. 16 are intended to be merely illustrative, and the present disclosure is not limited thereto. As depicted, the following layers and corresponding functions are provided:

Hardware and software layer 1602 includes hardware and software components. Examples of hardware components include mainframes, reduced instruction set computer (RISC) architecture based servers, servers, blade servers, storage devices, and networks and networking components. Examples of software components include network application server software and database software.

Virtualization layer 1604 provides an abstraction layer from which the following exemplary virtual entities may be provided: virtual servers; virtual storage; virtual networks, including virtual private networks; virtual applications; and virtual clients.

Management layer 1606 provides the exemplary functions described below. Resource provisioning provides dynamic procurement of computing resources and other resources that are utilized to perform tasks within the Cloud computing environment. Metering and Pricing provide cost tracking as resources are utilized within the cloud computing environment, and billing or invoicing for consumption of these resources. In one example, these resources may comprise application software licenses. Security provides identity verification for users and tasks, as well as protection for data and other resources. The user portal provides access to the Cloud computing environment for both users and system administrators. Service level management provides Cloud computing resource allocation and management such that service levels needed are met. Service Level Agreement (SLA) planning and fulfillment provide pre-arrangement for, and procurement of, Cloud computing resources for which a future requirement is anticipated in accordance with an SLA.

Workloads layer 1608 provides functionality for which the cloud computing environment is utilized. Examples of workloads and functions which may be provided from this layer include mapping and navigation; software development and lifecycle management; virtual classroom education delivery; data analytics processing; transaction processing; and resource credit management. As mentioned above, all of the foregoing examples described with respect to FIG. 16 are merely illustrative, and the present disclosure is not limited to these examples.

LISTING OF DRAWING ELEMENTS 100 process for using SSMVEP BCI
102 SSMVEP generated stimulus
104 environmental stimulus
106 block
108 block
110 block
112 decision block
114 block
116 decision block
118 block
200 exemplary SSVEP pattern and variation
202 base SSVEP pattern
204 SSVEP image on
206 SSVEP image off
300 exemplary SSMVEP pattern and variations
302 base SSMVEP pattern
304 base SSMVEP image
306 SSMVEP image with a different pattern density
308 SSMVEP image with a different size
310 rotated SSMVEP image
400 binocular projections for SSVEP BCI interaction
402 non-active background
404 active background
500 binocular projections for SSMVEP BCI interaction
600 AR-OST BCI configuration
602 user
604 AR-OST
606 AR-OST shield
608 frame
610 smart device slot
612 smart device
614 strap
616 BCI
618 EEG electrode
620 monitor
700 projections for SSVEP BCI use with AR-OST
702 monitor display
704 AR-OST shield display
800 projections for SSMVEP BCI use with AR-OST
802 monitor display
804 AR-OST shield display
806 user view through AR-OST shield
808 user's environment
900 C-CNN process
902 input
904 convolution
906 batch normalization ReLU activation dropout
908 convolution
910 batch normalization ReLU activation dropout
912 output
1000 IC states and NC states
1002 break period
1004 cue period
1006 stimulation period
1008 IC state
1010 NC state
1100a SSVEP 8 Hz results
1100b SSMVEP 8 Hz results
1100c SSVEP 10 Hz results
1100d SSMVEP 10 Hz results
1100e SSVEP 12 Hz results
1100f SSMVEP 12 Hz results
1100g SSVEP 15 Hz results
1100h SSMVEP 15 Hz results
1102 NB peak response
1104 AB peak response
1106 NB peak response
1108 AB peak response
1110 NB peak response
1112 AB peak response
1114 NB peak response
1116 AB peak response
1118 NB peak response
1120 AB peak response
1122 NB peak response
1124 AB peak response
1126 NB peak response
1128 AB peak response
1130 NB peak response
1132 AB peak response
1200 system
1202 environment
1204 environmental stimulus
1206 sensors
1208 wearable biosignal sensing device
1210 smart device
1212 context module
1214 user application
1216 requested stimuli data
1218 other context data
1220 rendering device
1222 user physiology
1224 biosensors
1226 BCI
1228 signal conditioning
1230 intentional control signal detection
1232 classifier
1234 further processing
1236 biosignals
1238 modified stimulus
1240 environmental stimuli data
1242 manual intention override
1244 current device context state data and requests for other device context state data
1246 response for recommended device context state and notifications and data for new stimuli
1248 classified selection
1250 cloud server
1252 context manager
1254 model modification process
1256 rendered stimulus
1258 user physical response
1260 internal sensor
1262 external sensor
1264 sensor data
1266 user's physical state and actions
1268 user
1300 classifier model modification
1302 machine learning model transmission controller
1304 model modification process
1306 local data records
1308 data records
1310 request for new model
1312 request and receive model specifications and initial parameters
1314 machine learning model
1316 predicted stimuli selected and associated metrics
1318 biosignal data and model parameters 1320 new state data and updated state data
1322 new machine learning models and updated machine learning models
1400 smart device
1402 system memory
1404 processing units
1406 Random access memory (RAM)
1408 I/O interfaces
1410 cache memory
1412 external devices
1414 display
1416 network adapter
1418 storage system
1420 program/utility
1422 program modules
1424 bus
1426 sensors
1428 actuators
1500 cloud computing system
1502 laptop
1504 desktop computer
1600 cloud computing functional abstraction layers
1602 hardware and software layer
1604 virtualization layer
1606 management layer
1608 workloads layer Various functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

Within this disclosure, different entities (which may variously be referred to as "units," "circuits," other components, etc.) may be described or claimed as "configured" to perform one or more tasks or operations. This formulation—[entity] configured to [perform one or more tasks]—is used herein to refer to structure (i.e., something physical, such as an electronic circuit). More specifically, this formulation is used to indicate that this structure is arranged to perform the one or more tasks during operation. A structure may be said to be "configured to" perform some task even if the structure is not currently being operated. A "credit distribution circuit configured to distribute credits to a plurality of processor cores" is intended to cover, for example, an integrated circuit that has Circuitry that performs this function during operation, even if the integrated circuit in question is not currently being used (e.g., a power supply is not connected to it). Thus, an entity described or recited as "configured to" perform some task refers to something physical, such as a device, circuit, memory storing program instructions executable to implement the task, etc. This phrase is not used herein to refer to something intangible.

The term "configured to" is not intended to mean "configurable to." An unprogrammed field programmable gate array (FPGA), for example, would not be considered to be "configured to" perform some specific function, although it may be "configurable to" perform that function after programming.

Reciting in the appended claims that a structure is "configured to" perform one or more tasks is expressly intended not to invoke 35 U.S.C. § 112(f) for that claim element. Accordingly, claims in this application that do not otherwise include the "means for" [performing a function] construct should not be interpreted under 35 U.S.C. § 112(f).

As used herein, the term "based on" is used to describe one or more factors that affect a determination. This term does not foreclose the possibility that additional factors may affect the determination. That is, a determination may be solely based on specified factors or based on the specified factors as well as other, unspecified factors. Consider the phrase "determine A based on B." This phrase specifies that B is a factor that is used to determine A or that affects the determination of A. This phrase does not foreclose that the determination of A may also be based on some other factor, such as C. This phrase is also intended to cover an embodiment in which A is determined based solely on B. As used herein, the phrase "based on" is synonymous with the phrase "based at least in part on."

As used herein, the phrase "in response to" describes one or more factors that trigger an effect. This phrase does not foreclose the possibility that additional factors may affect or otherwise trigger the effect. That is, an effect may be solely in response to those factors, or may be in response to the specified factors as well as other, unspecified factors. Consider the phrase "perform A in response to B." This phrase specifies that B is a factor that triggers the performance of A. This phrase does not foreclose that performing A may also be in response to some other factor, such as C. This phrase is also intended to cover an embodiment in which A is performed solely in response to B.

As used herein, the terms "first," "second," etc. are used as labels for nouns that they precede and do not imply any type of ordering (e.g., spatial, temporal, logical, etc.), unless stated otherwise. For example, in a register file having eight registers, the terms "first register" and "second register" may be used to refer to any two of the eight registers, and not, for example, just logical registers 0 and 1.

When used in the claims, the term "or" is used as an inclusive or and not as an exclusive or. For example, the phrase "at least one of x, y, or z" means any one of x, y, and z, as well as any combination thereof.

Having thus described illustrative embodiments in detail, it will be apparent that modifications and variations are possible without departing from the scope of the disclosed solution as claimed. The scope of disclosed subject matter is not limited to the depicted embodiments but is rather set forth in the following Claims.

Terms used herein should be accorded their ordinary meaning in the relevant arts, or the meaning indicated by their use in context, but if an express definition is provided, that meaning controls.

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, systems, methods and media for carrying out the several purposes of the disclosed subject matter. It is important, therefore, that the claims be regarded as including such equivalent constructions insofar as they do not depart from the spirit and scope of the disclosed subject matter.

What is claimed is:

1. A method comprising:
   receiving one or more requested stimuli data from a user application on a smart device;
   receiving at least one of sensor data and other context data, wherein the sensor data includes environmental stimuli from a surrounding environment and the other context data includes data that is un-sensed;
   transforming at least a portion of the requested stimuli data, into modified stimuli, based at least in part on at least one of the sensor data and the other context data;
   presenting the modified stimuli and the environmental stimuli to the user with a rendering device configured to mix the modified stimuli and the environmental stimuli, thereby resulting in rendered stimuli;
   receiving biosignals from the user, generated in response to the rendered stimuli, on a wearable biosignal sensing device;
   classifying the received biosignals using a classifier based on the modified stimuli, resulting in a classified selection; and
   returning the classified selection to the user application.

2. The method of claim 1, further comprising, after receiving the biosignals from the user:
   determining whether to send the received biosignals to the classifier by using at least one of:
     the existence of an intentional control signal, wherein determination of the existence of the intentional control signal includes at least one of:
       detecting a manual intention override signal from the smart device; and
       determining, at least in part, from the received biosignals that the user is intending to fixate on at least one of the rendered stimuli; and
     the absence of the intentional control signal;
   on condition the intentional control signal exists:
     sending the received biosignals, to the classifier; and
   on condition the intentional control signal is absent:
     continue receiving the received biosignals from the user.

3. The method of claim 1, wherein the modified stimuli is based in part on determining a device context state using at least one of the sensor data and the other context data.

4. The method of claim 1, wherein presenting the modified stimuli and the environmental stimuli to the user includes rendering the modified stimuli and the environmental stimuli using at least one of a visual device, a haptic device, and an auditory device sensed by the user.

5. The method of claim 1, wherein the modified stimuli include steady-state motion visually evoked potential stimuli, and presenting the modified stimuli and the environmental stimuli to the user includes rendering the modified stimuli and the environmental stimuli on an augmented reality optical see-through (AR-OST) device associated with the smart device.

6. The method of claim 1, wherein the at least one of the sensor data and the other context data includes at least one of:
   environmental data, body-mounted sensor data, connected ambulatory device data, location specific connected device data, and network connected device data.

7. The method of claim 1, further comprising:
   receiving, by a cloud server, the classified selection from the classifier, the cloud server including:
     a context manager;
     a machine learning model, used by the smart device to facilitate classification of the received biosignals by the classifier; and
   at least one model modification process for modifying the machine learning model;
   receiving, by the context manager, at least one of current context state data and requests for other state data;
   receiving, by the at least one model modification process, at least one of new state data and updated state data from the context manager; and
   updating the machine learning model using the at least one model modification process and at least one of the classified selection, the new state data, and the updated state data.

8. The method of claim 7, further comprising:
   sending an updated machine learning model, from the cloud server to the smart device; and
   transmitting the updated machine learning model to the classifier using a machine learning model transmission controller on the smart device.

9. The method of claim 8, further comprising:
   requesting a new machine learning model from the cloud server, by a context module on the smart device using the machine learning model transmission controller;
   receiving, by the smart device, the new machine learning model from the cloud server; and
   transmitting the new machine learning model to the classifier.

10. The method of claim 1, further comprising a context manager on a cloud server, wherein the context manager provides additional context information to the smart device.

11. A system comprising:
    a smart device;
    a rendering device;
    a wearable biosignal sensing device on a user;
    a processor; and
    a memory storing instructions that, when executed by the processor, configure the system to:
      receive one or more requested stimuli data from a user application on the smart device;
      receive at least one of sensor data and other context data, wherein the sensor data includes environmental stimuli from a surrounding environment and the other context data includes data that is un-sensed;
      transform at least a portion of the requested stimuli data, into modified stimuli, based at least in part on at least one of the sensor data and the other context data;
      present the modified stimuli and the environmental stimuli to the user with the rendering device configured to mix the modified stimuli and the environmental stimuli, thereby resulting in rendered stimuli;

receive biosignals from the user, generated in response to the rendered stimuli, on the wearable biosignal sensing device;
classify the received biosignals using a classifier based on the modified stimuli, resulting in a classified selection; and
return the classified selection to the user application.

12. The system of claim 11, wherein the instructions further configure the system to, after receiving the biosignals from the user:
determine whether to send the received biosignals to the classifier by using at least one of:
the existence of an intentional control signal, wherein determination of the existence of the intentional control signal includes at least one of:
detect a manual intention override signal from the smart device; and
determine, at least in part, from received biosignals that the user is intending to fixate on at least one of the rendered stimuli; and
the absence of the intentional control signal;
on condition the intentional control signal exists:
send the received biosignals, to the classifier; and
on condition the intentional control signal is absent:
continue to receive the received biosignals from the user.

13. The system of claim 11, wherein the modified stimuli is based in part on determining a device context state using at least one of the sensor data and the other context data.

14. The system of claim 11, wherein presenting the modified stimuli and the environmental stimuli to the user includes rendering the modified stimuli and the environmental stimuli using at least one of a visual device, a haptic device, and an auditory device sensed by the user.

15. The system of claim 11, wherein the modified stimuli include steady-state motion visually evoked potential stimuli, and presenting the modified stimuli and the environmental stimuli to the user includes rendering the modified stimuli and the environmental stimuli on an augmented reality optical see-through (AR-OST) device associated with the smart device.

16. The system of claim 11, wherein the at least one of the sensor data and the other context data includes at least one of:
environmental data, body-mounted sensor data, connected ambulatory device data, location specific connected device data, and network connected device data.

17. The system of claim 11, wherein the instructions further configure the system to:
receive, by a cloud server, the classified selection from the classifier,
the cloud server including:
a context manager;
a machine learning model, used by the smart device to facilitate classification of the received biosignals by the classifier; and
at least one model modification process for modifying the machine learning model;
receive, by the context manager, at least one of current context state data, and requests for other state data;
receive, by the at least one model modification process, at least one of new state data, and updated state data from the context manager; and
update the machine learning model using the at least one model modification process and at least one of the classified selection, the new state data, and the updated state data.

18. The system of claim 17, wherein the instructions further configure the system to:
send an updated machine learning model, by the cloud server to the smart device; and
transmit the updated machine learning model to the classifier using a machine learning model transmission controller on the smart device.

19. The system of claim 18, wherein the instructions further configure the system to:
request a new machine learning model from the cloud server, by a context module on the smart device using the machine learning model transmission controller;
receive, by the smart device, the new machine learning model from the cloud server; and
transmit the new machine learning model to the classifier.

20. A method comprising:
receiving one or more requested stimuli data from a user application on a smart device;
receiving at least one of sensor data and other context data, wherein the sensor data includes environmental stimuli from a surrounding environment and the other context data includes data that is un-sensed;
transforming at least a portion of the requested stimuli data, into modified stimuli, based at least in part on at least one of the sensor data and the other context data, wherein the modified stimuli include steady-state motion visually evoked potential stimuli;
presenting the modified stimuli and the environmental stimuli to the user with a rendering device configured to mix the modified stimuli and the environmental stimuli, thereby resulting in rendered stimuli, wherein presenting the modified stimuli and the environmental stimuli to the user includes at least one of:
rendering the modified stimuli and the environmental stimuli using at least one of a visual device, a haptic device, and an auditory device sensed by the user; and
rendering the modified stimuli and the environmental stimuli on an augmented reality optical see-through (AR-OST) device associated with the smart device;
receiving biosignals from the user, generated in response to the rendered stimuli, on a wearable biosignal sensing device;
determining whether to send the biosignals to a classifier by using at least one of:
the existence of an intentional control signal, wherein determination of the existence of the intentional control signal includes at least one of:
detecting a manual intention override signal from the smart device; and
determining, at least in part, from received biosignals that the user is intending to fixate on at least one of the rendered stimuli; and
the absence of the intentional control signal;
on condition the intentional control signal exists:
sending the received biosignals, to the classifier; and
on condition the intentional control signal is absent:
continue receiving the received biosignals from the user;
classifying the received biosignals using the classifier based on the modified stimuli, resulting in a classified selection; and
returning the classified selection to the user application.

* * * * *